US012760356B2

(12) United States Patent
Black et al.

(10) Patent No.: US 12,760,356 B2
(45) Date of Patent: Oct. 13, 2026

(54) COMPOSITIONS AND METHODS FOR CAPTURING AND AMPLIFYING TARGET POLYNUCLEOTIDES USING MODIFIED CAPTURE PRIMERS

(71) Applicant: Illumina, Inc., San Diego, CA (US)

(72) Inventors: Hayden Black, San Diego, CA (US); Esteban Armijo, San Diego, CA (US); Mathieu Lessard-Viger, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 383 days.

(21) Appl. No.: 18/000,663

(22) PCT Filed: Dec. 20, 2021

(86) PCT No.: PCT/US2021/064342
§ 371 (c)(1),
(2) Date: Dec. 2, 2022

(87) PCT Pub. No.: WO2022/140254
PCT Pub. Date: Jun. 30, 2022

(65) Prior Publication Data
US 2024/0011080 A1 Jan. 11, 2024

Related U.S. Application Data

(60) Provisional application No. 63/128,675, filed on Dec. 21, 2020.

(51) Int. Cl.
*C07H 21/02* (2006.01)
*C12Q 1/68* (2018.01)
*C12Q 1/6837* (2018.01)

(52) U.S. Cl.
CPC .................................. *C12Q 1/6837* (2013.01)

(58) Field of Classification Search
USPC .................. 435/6.1, 6.11, 91.1; 436/94, 501; 536/23.1, 24.3, 24.33
See application file for complete search history.

(56) References Cited

U.S. PATENT DOCUMENTS 8,652,810 B2 * 2/2014 Adessi .................. C12Q 1/686 435/6.12
2002/0037533 A1 * 3/2002 Civelli .................. G01N 33/74 435/7.1

(Continued)

FOREIGN PATENT DOCUMENTS

JP 2007222010 A 9/2007
WO 2008/046645 A2 4/2008

(Continued)

OTHER PUBLICATIONS

LNA design guidelines from Bio-Synthesis, Inc., pp. 1-3, published on Feb. 9, 2008.*

(Continued)

*Primary Examiner* — Frank W Lu

(57) ABSTRACT

A composition for capturing target polynucleotides at a surface of a substrate is provided. The composition may include a plurality of capture primers coupled to the surface of the substrate and including modified nucleic acids; and a plurality of orthogonal capture primers coupled to the surface of the substrate and including modified nucleic acids. The modified nucleic acids of the capture primers may include locked nucleic acid (LNA), peptide nucleic acid (PNA), or super T. The modified nucleic acids of the orthogonal capture primers may include locked nucleic acid (LNA), peptide nucleic acid (PNA), or super T.

23 Claims, 14 Drawing Sheets

Specification includes a Sequence Listing.

(56) References Cited

U.S. PATENT DOCUMENTS

2005/0053942 A1* 3/2005 Kauppinen .......... C12Q 1/6806
435/6.12
2014/0364322 A1* 12/2014 Hayden ................ C12Q 1/6844
435/6.12

FOREIGN PATENT DOCUMENTS

WO 2013/102090 A1 7/2013
WO 2014008447 A1 1/2014

OTHER PUBLICATIONS

Ørum et al., Detection of the Factor V Leiden Mutation by direct Allele-specific Hybridization of PCR Amplicons to Photoimmobilized Locked Nucleic Acids. Clinical Chemistry, 45, 1898-1905, 1999.*
International Search Report and Written Opinion for PCT/US2021/064342 dated Apr. 13, 2022; 14 pages.
Braasch et al., "Locked nucleic acid (LNA): fine-tuning the recognition of DNA and RNA" Chemistry & Biology 8:1-7 (2001).
Karkare et al., "Promising nucleic acid analogs and mimics: characteristic features and applications of Pna, Lna, and morpholino" Applied Microbiology and Biotechnology 71(5):575-586 (2006-05-09).
Levin et al., "Position-dependent effects of locked nucleic acid (LNA) on DNA sequencing and PCR primers" Nucleic Acids Research 34(20):e142 (2006).
Michikawa et al., "Reliable and Fast Allele-Specific Extension of 3'-LNA modified Oligonucleotides Covalently Immobilized on a Plastic Base, Combined with Biotin-dUTP Mediated Optical Detection", Analytical Sciences 22:1537-1545 (2006).
Misra et al., "Polyamide Nucleic Acid-DNA Chimera Lacking the Phosphate Backbone Are Novel Primers for Polymerase Reaction Catalyzed by DNA Polymerases" Biochemistry 37:1917-1925 (1998).
Owczarzy et al., "Stability and Mismatch Discrimination of Locked Nucleic Acid-DNA Duplexes" Biochemistry 50:9352-9367 (2011).
Robertson et al., "Locked Nucleic Acid Flow Cytometry-fluorescence in situ Hybridization (LNA flow-FISH): a Method for Bacterial Small RNA Detection," J. Vis. Exp. (59), e3655, doi: 10.379113655 (2012).

* cited by examiner

COMPOSITIONS AND METHODS FOR CAPTURING AND AMPLIFYING TARGET POLYNUCLEOTIDES USING MODIFIED CAPTURE PRIMERS

CROSS-REFERENCE TO RELATED APPLICATIONS

This application is a U.S. national phase application under 35 U.S.C. § 371 of PCT/US2021/064342 filed on Dec. 20, 2021 and entitled "Composition and Methods for Capturing and Amplifying Target Polynucleotides using Modified Capture Primers," which claims the benefit of U.S. Provisional Patent Application No. 63/128,675, filed Dec. 21, 2020 and entitled "Compositions and Methods for Capturing and Amplifying Target Polynucleotides Using Modified Capture Primers," the entire contents of each of which applications are incorporated by reference herein.

SEQUENCE LISTING

The instant application contains a Sequence Listing which has been submitted electronically in ASCII format and is hereby incorporated by reference in its entirety. Said ASCII copy is named IP-2054-PCT_SL.txt, is 4,174 bytes in size.

FIELD

This application relates to cluster amplification.

BACKGROUND

Cluster amplification is an approach to amplifying polynucleotides, for example for use in genetic sequencing. Target polynucleotides are captured by primers (e.g., P5 and P7 capture primers) coupled to a substrate surface in a flowcell, and form "seeds" at random locations on the surface. Cycles of amplification are performed to form clusters on the surface around each seed. The clusters include copies and complementary copies (which together may be referred as "amplicons") of the seed polynucleotides. For example, FIG. 1 schematically illustrates amplification of a polynucleotide on a substrate. Capture and amplification of a single seed 111 on substrate region 101 may result in monoclonal cluster 121 which may substantially fill the substrate region with amplicons of seed 111, and which readily may be used for sequencing-by-synthesis, or SBS (the dashed and dotted circles being intended to represent expansion of the cluster over time). In some circumstances, the substrate is patterned so as to define regions that bound different clusters, such as wells that may be filled with respective clusters.

SUMMARY

Examples provided herein are related to capturing and amplifying target polynucleotides using modified capture primers. Compositions and methods for performing such capture and amplification are disclosed.

In some examples, provided herein is a composition for capturing target polynucleotides at a surface of a substrate. The composition may include a plurality of capture primers coupled to the surface of the substrate. Each capture primer may include modified nucleic acids. The composition also may include a plurality of orthogonal capture primers coupled to the surface of the substrate. Each orthogonal capture primer may include modified nucleic acids.

In some examples, the modified nucleic acids of the capture primers include locked nucleic acid (LNA), peptide nucleic acid (PNA), or super T. In some examples, the capture primers further include deoxyribonucleic acid (DNA). In some examples, the modified nucleic acids and the DNA are distributed between a 5' end and a 3' end of the capture primers. In some examples, the modified nucleic acids are disposed at a 5' end of the capture primers and the DNA is disposed at a 3' end of the capture primers.

In some examples, the modified nucleic acids of the orthogonal capture primers include locked nucleic acid (LNA), peptide nucleic acid (PNA), or super T. In some examples, the orthogonal capture primers further include deoxyribonucleic acid (DNA). In some examples, the modified nucleic acids and the DNA are distributed between a 5' end and a 3' end of the capture primers. In some examples, the modified nucleic acids are disposed at a 5' end of the orthogonal capture primers and the DNA is disposed at a 3' end of the orthogonal capture primers.

In some examples, the composition further includes first target polynucleotides, each including a first adapter that is complementary to the capture primers, and a second adapter that is complementary to the orthogonal capture primers. The composition further may include second target polynucleotides that are complementary to respective ones of the first target polynucleotides.

In some examples, the first adapters of some of the first target polynucleotides are hybridized to respective ones of the capture primers to form first duplexes, and the second adapters of some of the first target polynucleotides are hybridized to respective ones of the orthogonal capture primers to form second duplexes. In some examples, the first and second duplexes each have a melting temperature (Tm) that is greater than a Tm of third duplexes that would be formed by hybridization of the second target polynucleotides to the respective ones of the first target polynucleotides to which the second target polynucleotides are complementary. In some examples, the first and second duplexes each have a Tm that is between about 80° C. and about 110° C. In some examples, the first and second duplexes each have a Tm that is between about 85° C. and about 105° C. In some examples, the first and second duplexes each have a Tm that is between about 90° C. and about 100° C.

In some examples, substantially none of the second target polynucleotides are hybridized in solution to any of the first target polynucleotides.

In some examples, the composition further includes about 1% to about 100% formamide (% v/v), or about 5% to about 80% formamide (% v/v).

In some examples, the composition further includes further includes about 100 to about 800 mM Na+, or about 200 to about 800 mM Na+.

In some examples, the capture primers are modified P5 capture primers, and the orthogonal capture primers are modified P7 capture primers.

In some examples, each of the capture primers includes between about five and about twenty of the modified nucleic acids, and each of the orthogonal capture primers includes between about five and about twenty of the modified nucleic acids.

In some examples, each of the capture primers includes at least about nine of the modified nucleic acids, and each of the orthogonal capture primers includes at least about nine of the modified nucleic acids; or each of the capture primers includes at least about twelve of the modified nucleic acids, and each of the orthogonal capture primers includes at least about twelve of the modified nucleic acids; or each of the capture primers includes at least about fifteen of the modified nucleic acids, and each of the orthogonal capture primers includes at least about fifteen of the modified nucleic acids.

In some examples, provided herein is a method for capturing and amplifying target polynucleotides at a surface of a substrate. The method may include contacting a composition with a fluid. The composition may include a plurality of capture primers coupled to the surface of the substrate, each capture primer including modified nucleic acids; and a plurality of orthogonal capture primers coupled to the surface of the substrate, each orthogonal capture primer including modified nucleic acids. The fluid may include first target polynucleotides, each including a first adapter that is complementary to the capture primers and a second adapter that is complementary to the orthogonal capture primers; and second target polynucleotides that are complementary to respective ones of the first target polynucleotides. The method may include, while inhibiting hybridization of the second target polynucleotides to the first target polynucleotides in the fluid: hybridizing the first adapters of some of the first target polynucleotides to respective ones of the capture primers to form first duplexes; hybridizing the second adapters of some of the first target polynucleotides to respective ones of the orthogonal capture primers to form second duplexes; and then amplifying the first target polynucleotides, the amplifying including generating respective amplicons of the first target polynucleotides.

In some examples, the modified nucleic acids of the capture primers include locked nucleic acid (LNA), peptide nucleic acid (PNA), or super T. In some examples, the capture primers further include deoxyribonucleic acid (DNA). In some examples, the modified nucleic acids and the DNA are distributed between a 5' end and a 3' end of the capture primers. In some examples, the modified nucleic acids are disposed at a 5' end of the capture primers and the DNA is disposed at a 3' end of the capture primers.

In some examples, the modified nucleic acids of the orthogonal capture primers include locked nucleic acid (LNA), peptide nucleic acid (PNA), or super T. In some examples, the orthogonal capture primers further include deoxyribonucleic acid (DNA). In some examples, the modified nucleic acids and the DNA are distributed between a 5' end and a 3' end of the capture primers. In some examples, the modified nucleic acids are disposed at a 5' end of the orthogonal capture primers and the DNA is disposed at a 3' end of the orthogonal capture primers.

In some examples, the first and second duplexes each have a melting temperature (Tm) that is greater than a Tm of third duplexes that would be formed by hybridization of the second target polynucleotides to the respective ones of the first target polynucleotides to which the second target polynucleotides are complementary. In some examples, the first and second duplexes each have a Tm that is between about 80° C. and about 110° C. In some examples, the first and second duplexes each have a Tm that is between about 85° C. and about 105° C. In some examples, the first and second duplexes each have a Tm that is between about 90° C. and about 100° C.

In some examples, substantially none of the second target polynucleotides are hybridized in solution to any of the first target polynucleotides.

In some examples, the hybridizing is performed in about 1% to about 100% formamide (% v/v), or in about 5% to about 80% formamide (% v/v).

In some examples, the hybridizing is performed in about 100 to about 800 mM Na+, or in about 200 to about 800 mM Na+.

In some examples, the capture primers are modified P5 capture primers, and the orthogonal capture primers are modified P7 capture primers.

In some examples, each of the capture primers includes between about five and about twenty of the modified nucleic acids, and each of the orthogonal capture primers includes between about five and about twenty of the modified nucleic acids. In some examples, each of the capture primers includes at least about nine of the modified nucleic acids, and each of the orthogonal capture primers includes at least about nine of the modified nucleic acids; or each of the capture primers includes at least about twelve of the modified nucleic acids, and each of the orthogonal capture primers includes at least about twelve of the modified nucleic acids; or each of the capture primers includes at least about fifteen of the modified nucleic acids, and each of the orthogonal capture primers includes at least about fifteen of the modified nucleic acids.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

DETAILED DESCRIPTION

Figure 1:
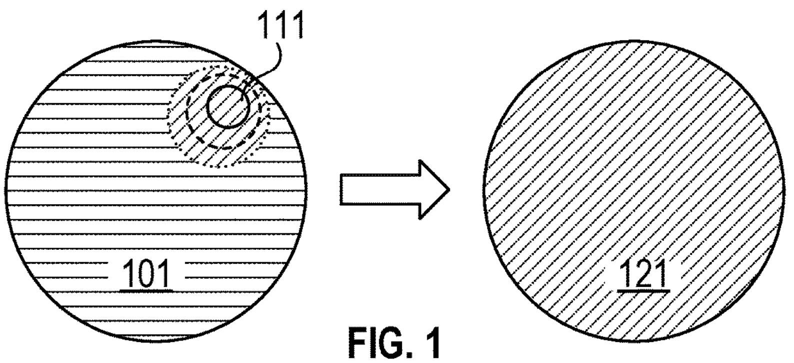
FIG. 1 schematically illustrates amplification of a polynucleotide on a substrate.

Examples provided herein are related to capturing and amplifying polynucleotides using modified capture primers. Compositions and methods for performing such capture and amplification are disclosed.

The modified capture primers provided herein may hybridize more strongly with target polynucleotides than do previously known capture primers, and as such may enhance the efficiency with which target polynucleotides are captured on a substrate. Illustratively, because of the stronger binding, lower concentrations of target polynucleotides may be used to prepare clusters on a substrate, as compared to previously known capture primers. For example, in a manner such as described further below with reference to FIGS. 2A-2C, polynucleotide capture and amplification using previously known primers may be performed under conditions in which surface hybridization and solution-based annealing operate as competing processes that render some of the polynucleotides unavailable for capture or amplification. In comparison, in a manner such as described with reference to FIGS. 3A-3H, 4, 5A-5C, and 6, the present capture primers allow for polynucleotide capture and amplification to be performed under conditions that reduce or inhibit solution-based annealing as a competing process, and as such may substantially increase the availability of polynucleotides for capture and amplification, may permit use of higher concentrations of target polynucleotides to prepare clusters on a substrate, as compared to previously known capture primers, and may reduce the overall seeding time.

First, some terms used herein will be briefly explained. Then, some example compositions and example methods for capturing and amplifying polynucleotides using the present capture primers will be described.

Terms

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The terms "substantially," "approximately," and "about" used throughout this specification are used to describe and account for small fluctuations, such as due to variations in processing. For example, they may refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to 0.1%, such as less than or equal to ±0.05%.

As used herein, "hybridize" is intended to mean noncovalently associating a first polynucleotide to a second polynucleotide along the lengths of those polynucleotides to form a double-stranded "duplex." For instance, two DNA polynucleotide strands may associate through complementary base pairing. The strength of the association between the first and second polynucleotides increases with the complementarity between the sequences of nucleotides within those polynucleotides. The strength of hybridization between polynucleotides may be characterized by a temperature of melting (Tm) at which 50% of the duplexes have polynucleotide strands that disassociate from one another. Polynucleotides that are "partially" hybridized to one another means that they have sequences that are complementary to one another, but such sequences are hybridized with one another along only a portion of their lengths to form a partial duplex. Polynucleotides with an "inability" to hybridize include those which are physically separated from one another such that an insufficient number of their bases may contact one another in a manner so as to hybridize with one another.

As used herein, the term "nucleotide" is intended to mean a molecule that includes a sugar moiety, a backbone component that includes at least one phosphate group, and in some examples also includes a nucleobase. A nucleotide that lacks a nucleobase may be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

As used herein, the term "nucleotide" also is intended to encompass any "nucleotide analogue" which is intended to refer to a type of nucleotide that includes a modified nucleobase, sugar moiety, and/or backbone component (such as a phosphate or amide) compared to naturally occurring nucleotides. Nucleotide analogues also may be referred to as "modified nucleic acids." Example modified nucleobases include inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate. The backbone components of nucleotides may include any suitable number of phosphates, e.g., three, four, five, six, or more than six phosphates. Nucleotide analogues also include locked nucleic acids (LNA), peptide nucleic acids (PNA), and 5-hydroxylbutynl-2'-deoxyuridine ("super T"). LNA includes an RNA-like backbone in which ribose moieties include an additional bridge connecting the 2' oxygen and 4' carbon. PNA includes a backbone that includes repeating N-(2-aminoethyl)-glycine units linked by peptide bonds, and nucleobases that are coupled to the backbone via a methylene bridge and carbonyl group. Super T includes a 5-hydroxybutynl-2'-deoxyuridine nucleobase. Example structures for LNA, PNA, and super T are shown below:

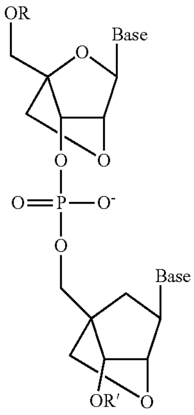

Locked nucleic acid (LNA)

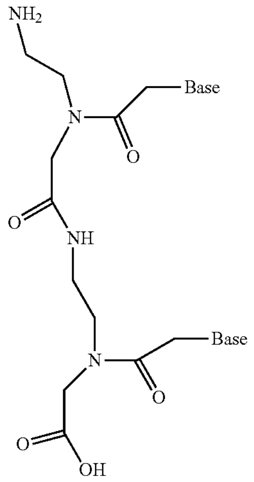

Peptide nucleic acid (PNA)

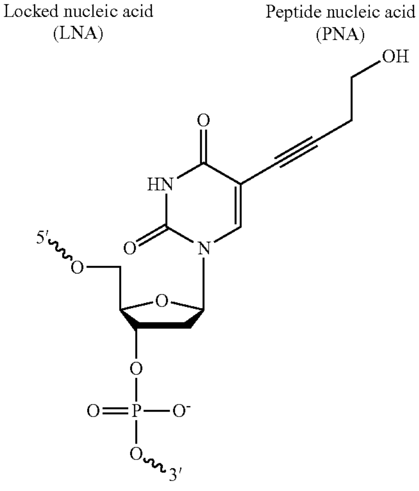

Super T

As used herein, the term "polynucleotide" refers to a molecule that includes a sequence of nucleotides that are bonded to one another. A polynucleotide is one nonlimiting example of a polymer. Examples of polynucleotides include deoxyribonucleic acid (DNA), ribonucleic acid (RNA), and analogues thereof such as locked nucleic acids (LNA) and peptide nucleic acids (PNA). A polynucleotide may be a single stranded sequence of nucleotides, such as RNA or single stranded DNA, a double stranded sequence of nucleotides, such as double stranded DNA, or may include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. Polynucleotides may include non-naturally occurring DNA, such as enantiomeric DNA, LNA, or PNA. The precise sequence of nucleotides in a polynucleotide may be known or unknown. The following are examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing. A polynucleotide may have a "chimera" structure that includes adjoined sections of different types of polynucleotides, such as adjoined sections of DNA and PNA, of DNA and RNA, of PNA and RNA, or the like.

As used herein, a "polymerase" is intended to mean an enzyme having an active site that assembles polynucleotides by polymerizing nucleotides into polynucleotides. A polymerase can bind a primed single stranded target polynucleotide, and can sequentially add nucleotides to the growing primer to form a "complementary copy" polynucleotide having a sequence that is complementary to that of the target polynucleotide. Another polymerase, or the same polymerase, then can form a copy of the target nucleotide by forming a complementary copy of that complementary copy polynucleotide. Any of such copies may be referred to herein as "amplicons." DNA polymerases may bind to the target polynucleotide and then move down the target polynucleotide sequentially adding nucleotides to the free hydroxyl group at the 3' end of a growing polynucleotide strand (growing amplicon). DNA polymerases may synthesize complementary DNA molecules from DNA templates and RNA polymerases may synthesize RNA molecules from DNA templates (transcription). Polymerases may use a short RNA or DNA strand (primer), to begin strand growth. Some polymerases may displace the strand upstream of the site where they are adding bases to a chain. Such polymerases may be said to be strand displacing, meaning they have an activity that removes a complementary strand from a template strand being read by the polymerase. Exemplary polymerases having strand displacing activity include, without limitation, the large fragment of Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the term "primer" is defined as a polynucleotide to which nucleotides may be added via a free 3' OH group. A primer may include a 3' block preventing polymerization until the block is removed. A primer may include a modification at the 5' terminus to allow a coupling reaction or to couple the primer to another moiety. A primer may include one or more moieties, such as 8-oxo-G, which may be cleaved under suitable conditions, such as UV light, chemistry, enzyme, or the like. The primer length may be any suitable number of bases long and may include any suitable combination of natural and non-natural nucleotides. A target polynucleotide may include an "adapter" that hybridizes to (has a sequence that is complementary to) a primer, and may be amplified so as to generate a complementary copy polynucleotide by adding nucleotides to the free 3' OH group of the primer. A "capture primer" is intended to mean a primer that is coupled to the substrate and may hybridize to a first adapter of the target polynucleotide, while an "orthogonal capture primer" is intended to mean a primer that is coupled to the substrate and may hybridize to a second adapter of that target polynucleotide. The first adapter may have a sequence that is complementary to that of the capture primer, and the second adapter may have a sequence that is complementary to that of the orthogonal capture primer. A capture primer and an orthogonal capture primer may have different and independent sequences than one another. Additionally, a capture primer and an orthogonal capture primer may differ from one another in at least one other property. For example, the capture primer and the orthogonal capture primer may have different lengths than one another; either the capture primer or the orthogonal capture primer may include a non-nucleic acid moiety (such as a blocking group or excision moiety) that the other of the capture primer or the orthogonal capture primer lacks; or any suitable combination of such properties. A "modified capture primer" is a capture primer, or orthogonal capture primer, that includes a plurality of nucleic acid analogues such as, but not limited to, LNA, PNA, or super T. A modified capture primer additionally may include a plurality of naturally occurring nucleic acids such as, but not limited to, DNA.

As used herein, the term "substrate" refers to a material used as a support for compositions described herein. Example substrate materials may include glass, silica, plastic, quartz, metal, metal oxide, organo-silicate (e.g., polyhedral organic silsesquioxanes (POSS)), polyacrylates, tantalum oxide, complementary metal oxide semiconductor (CMOS), or combinations thereof. An example of POSS can be that described in Kehagias et al., Microelectronic Engineering 86 (2009), pp. 776-778, which is incorporated by reference in its entirety. In some examples, substrates used in the present application include silica-based substrates, such as glass, fused silica, or other silica-containing material. In some examples, substrates may include silicon, silicon nitride, or silicone hydride. In some examples, substrates used in the present application include plastic materials or components such as polyethylene, polystyrene, poly (vinyl chloride), polypropylene, nylons, polyesters, polycarbonates, and poly(methyl methacrylate). Example plastics materials include poly(methyl methacrylate), polystyrene, and cyclic olefin polymer substrates. In some examples, the substrate is or includes a silica-based material or plastic material or a combination thereof. In particular examples, the substrate has at least one surface comprising glass or a silicon-based polymer. In some examples, the substrates may include a metal. In some such examples, the metal is gold. In some examples, the substrate has at least one surface comprising a metal oxide. In one example, the surface comprises a tantalum oxide or tin oxide. Acrylamides, enones, or acrylates may also be utilized as a substrate material or component. Other substrate materials may include, but are not limited to gallium arsenide, indium phosphide, aluminum, ceramics, polyimide, quartz, resins, polymers and copolymers. In some examples, the substrate and/or the substrate surface may be, or include, quartz. In some other examples, the substrate and/or the substrate surface may be, or include, semiconductor, such as GaAs or ITO. The foregoing lists are intended to be illustrative of, but not limiting to the present application. Substrates may comprise a single material or a plurality of different materials. Substrates may be composites or laminates. In some examples, the substrate comprises an organo-silicate material. Substrates may be flat, round, spherical, rod-shaped, or any other suitable shape. Substrates may be rigid or flexible. In some examples, a substrate is a bead or a flow cell.

In some examples, a substrate includes a patterned surface. A "patterned surface" refers to an arrangement of different regions in or on an exposed layer of a substrate. For example, one or more of the regions may be features where one or more capture primers are present. The features can be separated by interstitial regions where capture primers are not present. In some examples, the pattern may be an x-y format of features that are in rows and columns. In some examples, the pattern may be a repeating arrangement of features and/or interstitial regions. In some examples, the pattern may be a random arrangement of features and/or interstitial regions. In some examples, substrate includes an array of wells (depressions) in a surface. The wells may be provided by substantially vertical sidewalls. Wells may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface of a substrate may include wells in an array of wells (e.g., microwells or nanowells) on glass, silicon, plastic or other suitable material(s) with patterned, covalently-linked gel such as poly(N-(5-azidoacetamidylpentyl) acrylamide-co-acrylamide) (PAZAM). The process creates gel pads used for sequencing that may be stable over sequencing runs with a large number of cycles. The covalent linking of the polymer to the wells may be helpful for maintaining the gel in the structured features throughout the lifetime of the structured substrate during a variety of uses. However in many examples, the gel need not be covalently linked to the wells. For example, in some conditions silane free acrylamide (SFA) which is not covalently attached to any part of the structured substrate, may be used as the gel material.

In particular examples, a structured substrate may be made by patterning a suitable material with wells (e.g. microwells or nanowells), coating the patterned material with a gel material (e.g., PAZAM, SFA or chemically modified variants thereof, such as the azidolyzed version of SFA (azido-SFA)) and polishing the surface of the gel coated material, for example via chemical or mechanical polishing, thereby retaining gel in the wells but removing or inactivating substantially all of the gel from the interstitial regions on the surface of the structured substrate between the wells. Primers may be attached to gel material. A solution including a plurality of target polynucleotides (e.g., a fragmented human genome or portion thereof) may then be contacted with the polished substrate such that individual target polynucleotides will seed individual wells via interactions with primers attached to the gel material; however, the target polynucleotides will not occupy the interstitial regions due to absence or inactivity of the gel material. Amplification of the target polynucleotides may be confined to the wells because absence or inactivity of gel in the interstitial regions may inhibit outward migration of the growing cluster. The process is conveniently manufacturable, being scalable and utilizing conventional micro- or nano-fabrication methods.

A patterned substrate may include, for example, wells etched into a slide or chip. The pattern of the etchings and geometry of the wells may take on a variety of different shapes and sizes, and such features may be physically or functionally separable from each other. Particularly useful substrates having such structural features include patterned substrates that may select the size of solid particles such as microspheres. An exemplary patterned substrate having these characteristics is the etched substrate used in connection with BEAD ARRAY technology (Illumina, Inc., San Diego, Calif.).

In some examples, a substrate described herein forms at least part of a flow cell or is located in or coupled to a flow cell. Flow cells may include a flow chamber that is divided into a plurality of lanes or a plurality of sectors. Example flow cells and substrates for manufacture of flow cells that may be used in methods and compositions set forth herein include, but are not limited to, those commercially available from Illumina, Inc. (San Diego, Calif.).

As used herein, the term “directly” and the like, when used in reference to a layer covering the surface of a substrate is intended to mean that the layer covers the substrate’s surface without a significant intermediate layer, such as, e.g., an adhesive layer or a polymer layer. Layers directly covering a surface may be attached to this surface through any chemical or physical interaction, including covalent bonds or non-covalent adhesion.

As used herein, the term “immobilized” when used in reference to a polynucleotide is intended to mean direct or indirect attachment to a substrate via covalent or non-covalent bond(s). In certain examples, covalent attachment may be used, or any other suitable attachment in which the polynucleotides remain stationary or attached to a substrate under conditions in which it is intended to use the substrate, for example, in polynucleotide amplification or sequencing. Polynucleotides to be used as capture primers or as target polynucleotides may be immobilized such that a 3-end is available for enzymatic extension and at least a portion of the sequence is capable of hybridizing to a complementary sequence. Immobilization may occur via hybridization to a surface attached oligonucleotide, in which case the immobilized oligonucleotide or polynucleotide may be in the 3'-5' orientation. Alternatively, immobilization may occur by means other than base-pairing hybridization, such as covalent attachment. Illustratively, a chemical functionality may be incorporated onto the 5' end of one of the present capture primers via a chemical linker. The chemical functionality on the capture primer is capable of attachment to the substrate surface via any suitable combination of one or more non-covalent interaction(s) (e.g., electrostatic, metal-ligand binding, hybridization, or the like) or covalent interaction(s) (e.g., copper click chemistry reactions, copper free click chemistry reactions, or the like).

As used herein, the term “array” refers to a population of substrate regions that may be differentiated from each other according to relative location. Different molecules (such as polynucleotides) that are at different regions of an array may be differentiated from each other according to the locations of the regions in the array. An individual region of an array may include one or more molecules of a particular type. For example, a substrate region may include a single target polynucleotide having a particular sequence, or a substrate region may include several polynucleotides having the same sequence (or complementary sequences thereof). The regions of an array respectively may include different features than one another on the same substrate. Exemplary features include without limitation, wells in a substrate, beads (or other particles) in or on a substrate, projections from a substrate, ridges on a substrate or channels in a substrate. The regions of an array respectively may include different regions on different substrates than each other. Different molecules attached to separate substrates may be identified according to the locations of the substrates on a surface to which the substrates are associated or according to the locations of the substrates in a liquid or gel. Exemplary arrays in which separate substrates are located on a surface include, without limitation, those having beads in wells.

As used herein, the term “plurality” is intended to mean a population of two or more different members. Pluralities may range in size from small, medium, large, to very large. The size of small plurality may range, for example, from a few members to tens of members. Medium sized pluralities may range, for example, from tens of members to about 100 members or hundreds of members. Large pluralities may range, for example, from about hundreds of members to about 1000 members, to thousands of members and up to tens of thousands of members. Very large pluralities may range, for example, from tens of thousands of members to about hundreds of thousands, a million, millions, tens of millions and up to or greater than hundreds of millions of members. Therefore, a plurality may range in size from two to well over one hundred million members as well as all sizes, as measured by the number of members, in between and greater than the above exemplary ranges. Exemplary polynucleotide pluralities include, for example, populations of about $1\times10^5$ or more, $5\times10^5$ or more, or $1\times10^6$ or more different polynucleotides. Accordingly, the definition of the term is intended to include all integer values greater than two. An upper limit of a plurality may be set, for example, by the theoretical diversity of polynucleotide sequences in a sample.

As used herein, the term “double-stranded,” when used in reference to a polynucleotide, is intended to mean that all or substantially all of the nucleotides in the polynucleotide are hydrogen bonded to respective nucleotides in a complementary polynucleotide. A “partially” double stranded polynucleotide may have at least about 10%, at least about 25%, at least about 50%, at least about 60%, at least about 70%, at least about 80%, at least about 90% or at least about 95% of its nucleotides, but fewer than all of its nucleotides, hydrogen bonded to nucleotides in a complementary polynucleotide.

As used herein, the term “single-stranded,” when used in reference to a polynucleotide, means that essentially none of the nucleotides in the polynucleotide are hydrogen bonded to a respective nucleotide in a complementary polynucleotide. A polynucleotide that has an “inability” to hybridize to another polynucleotide may be single-stranded.

As used herein, the term “target polynucleotide” is intended to mean a polynucleotide that is the object of an analysis or action, and may also be referred to as a “library polynucleotide,” “template polynucleotide,” or “library template.” The analysis or action includes subjecting the polynucleotide to capture, amplification, sequencing and/or other procedure. A target polynucleotide may include nucleotide sequences additional to a target sequence to be analyzed. For example, a target polynucleotide may include one or more adapters, including an adapter that functions as a primer binding site, that flank(s) a target polynucleotide sequence that is to be analyzed. A target polynucleotide hybridized to a capture primer may include nucleotides that extend beyond the 5' or 3' end of the capture oligonucleotide in such a way that not all of the target polynucleotide is amenable to extension. In particular examples, target polynucleotides may have different sequences than one another but may have first and second adapters that are the same as one another. The two adapters that may flank a particular target polynucleotide sequence may have the same sequence as one another, or complementary sequences to one another, or the two adapters may have different sequences. Thus, species in a plurality of target polynucleotides may include regions of known sequence that flank regions of unknown sequence that are to be evaluated by, for example, sequencing (e.g., SBS). In some examples, target polynucleotides carry an adapter at a single end, and such adapter may be located at either the 3' end or the 5' end the target polynucleotide. Target polynucleotides may be used without any adapter, in which case a primer binding sequence may come directly from a sequence found in the target polynucleotide.

The terms "polynucleotide" and "oligonucleotide" are used interchangeably herein. The different terms are not intended to denote any particular difference in size, sequence, or other property unless specifically indicated otherwise. For clarity of description, the terms may be used to distinguish one species of polynucleotide from another when describing a particular method or composition that includes several polynucleotide species.

As used herein, the term "amplicon," when used in reference to a polynucleotide, is intended to means a product of copying the polynucleotide, wherein the product has a nucleotide sequence that is substantially the same as, or is substantially complementary to, at least a portion of the nucleotide sequence of the polynucleotide. "Amplification" and "amplifying" refer to the process of making an amplicon of a polynucleotide. A first amplicon of a target polynucleotide may be a complementary copy. Additional amplicons are copies that are created, after generation of the first amplicon, from the target polynucleotide or from the first amplicon. A subsequent amplicon may have a sequence that is substantially complementary to the target polynucleotide or is substantially identical to the target polynucleotide. It will be understood that a small number of mutations (e.g., due to amplification artifacts) of a polynucleotide may occur when generating an amplicon of that polynucleotide.

A substrate region that includes substantially only amplicons of a given polynucleotide may be referred to as "monoclonal," while a substrate region that includes amplicons of polynucleotides having different sequences than one another may be referred to as "polyclonal." A polyclonal region of a substrate may include different subregions therein that respectively are monoclonal. Each such monoclonal region, whether within a larger polyclonal region or on its own, may correspond to a "cluster" generated from a "seed." The "seed" may refer to a single target polynucleotide, while the "cluster" may refer to a collection of amplicons of that target polynucleotide.

Compositions and Methods for Capturing and Amplifying Polynucleotides

Examples provided herein relate to compositions and methods capturing and amplifying target polynucleotides using modified capture primers that may be used under conditions that reduce or inhibit solution-based annealing while permitting the modified capture primers to capture target polynucleotides from solution. In comparison, previously known capture primers may be used under conditions in which solution-based annealing competes with capture of target polynucleotides from solution, and such competition reduces availability of the target polynucleotides for capture.

Figure 2A:
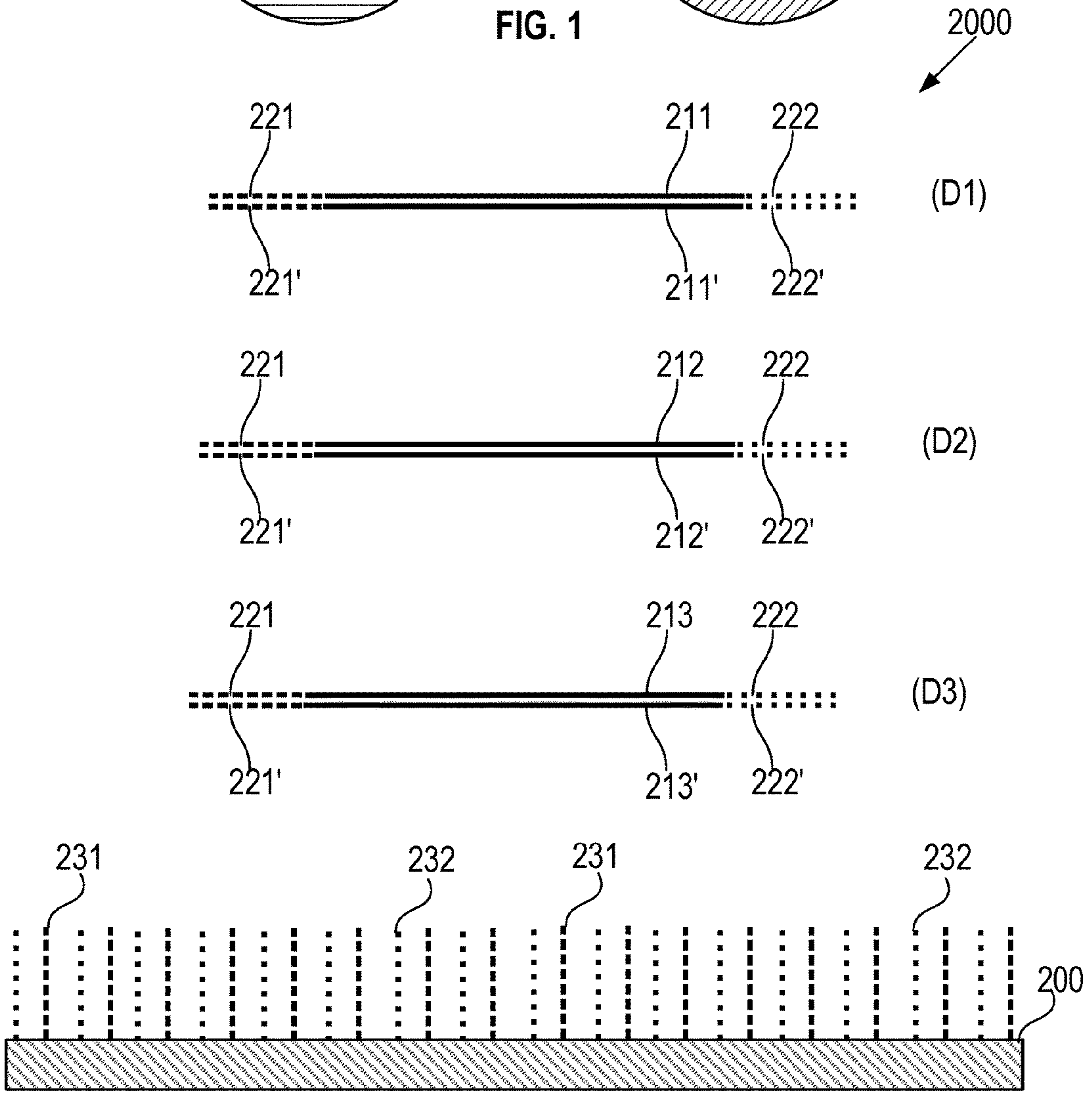
FIGS. 2A-2C schematically illustrate compositions and operations in a process flow for capture of polynucleotides on a substrate using previously known capture primers.
Figure 2B:
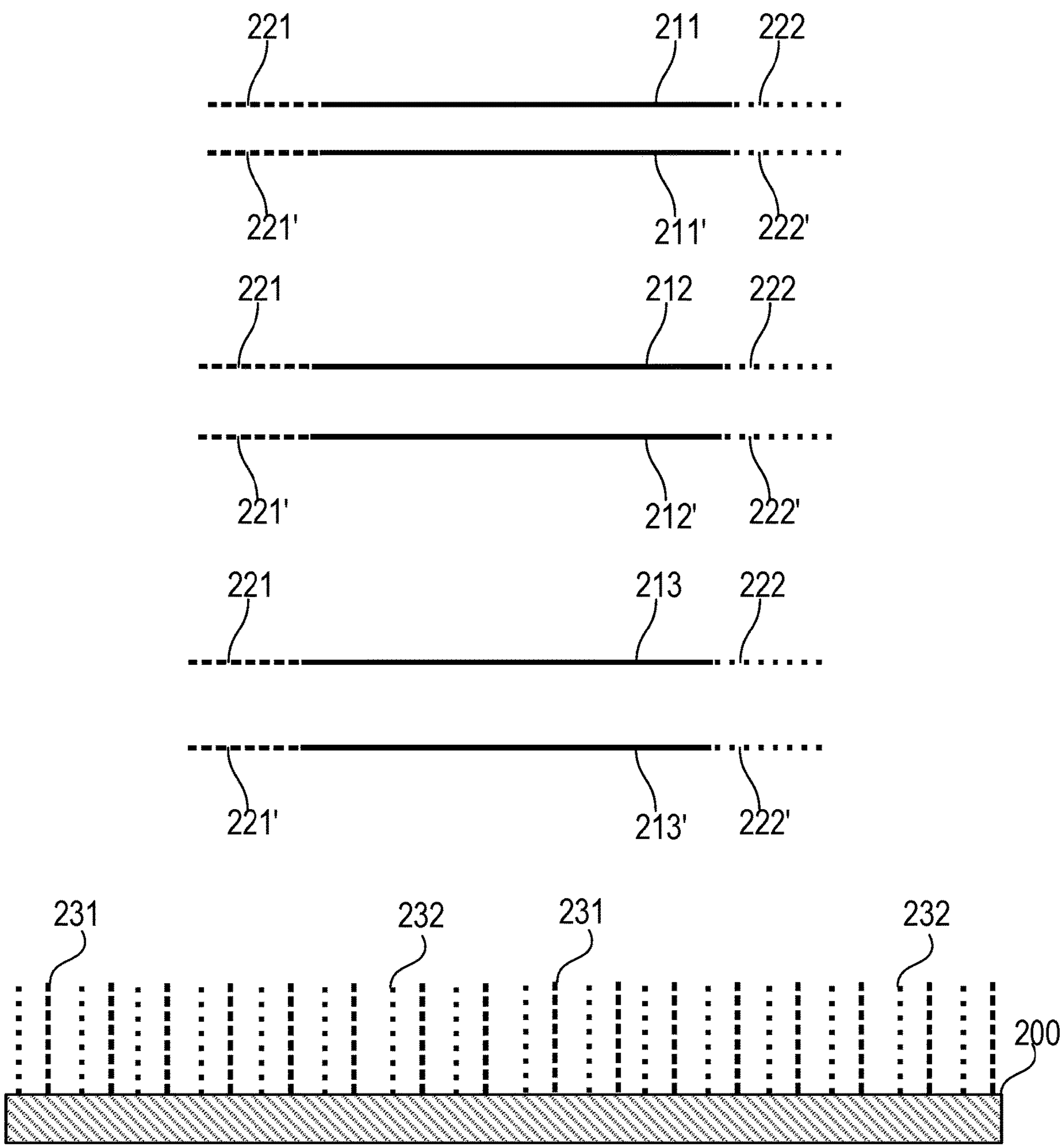
Figure 2C:
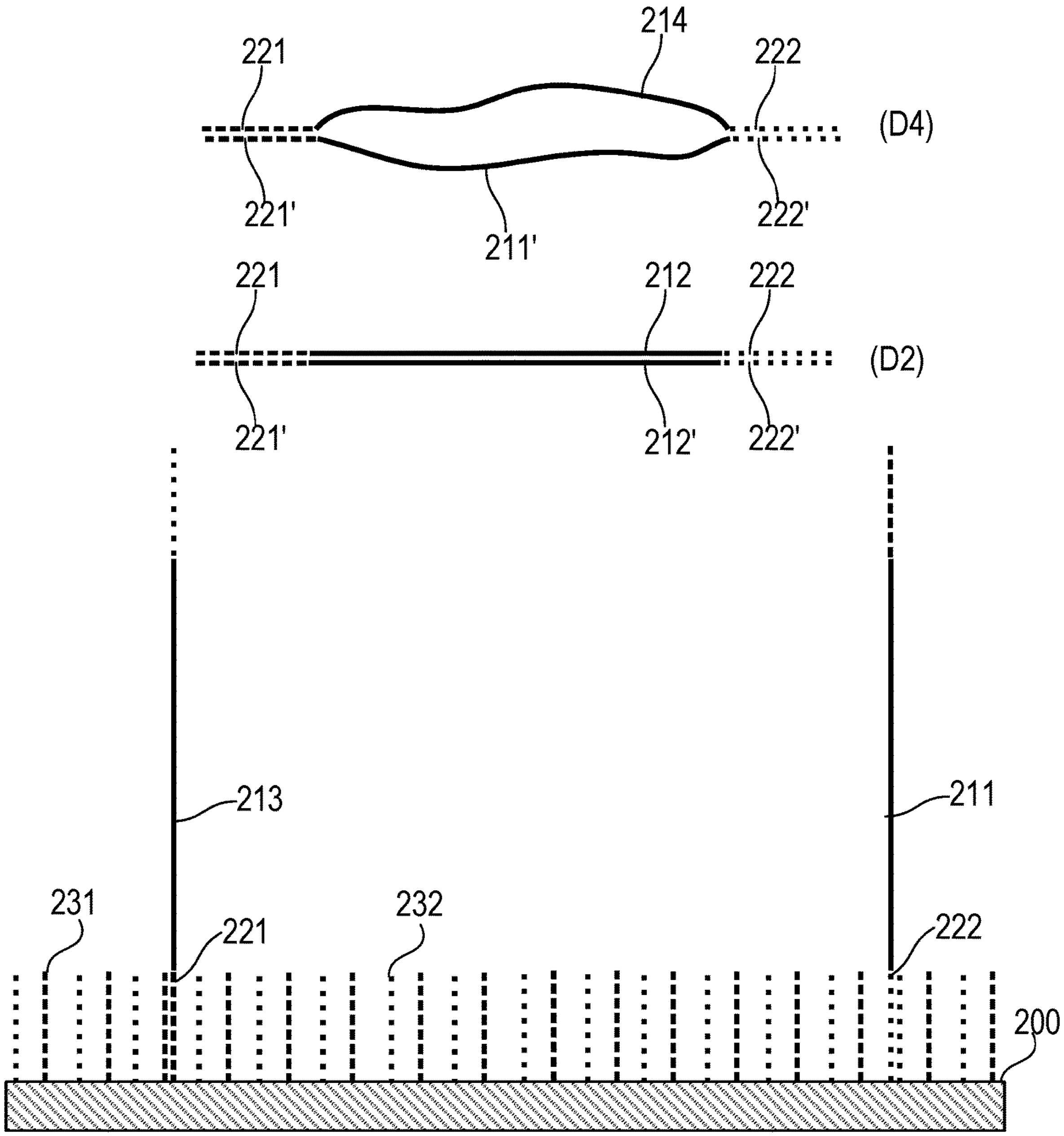

For example, FIGS. 2A-2C schematically illustrate compositions and operations in a process flow for capture of polynucleotides on a substrate using previously known capture primers. Composition 2000 illustrated in FIG. 2A includes substrate 200 having capture primers 231 and orthogonal capture primers 232 coupled thereto, as well as a fluid (solution) containing target polynucleotides, e.g., polynucleotides that it is intended to capture, amplify, and sequence using sequencing-by-synthesis (SBS). The target polynucleotides may include or may be provided in the form of duplexes (illustratively, duplexes D1, D2, and D3) between target polynucleotides having sequences that are complementary to one another. For example, duplex D1 may include a first target polynucleotide including sequence 211, first adapter 221, and second adapter 222, and a second target nucleotide that is complementary to the first target polynucleotide, e.g., including complementary sequence 211', first complementary adapter 221', and second complementary adapter 222'. Similarly, duplex D2 may include a first target polynucleotide including sequence 212, first adapter 221, and second adapter 222, and a second target nucleotide that is complementary to the first target polynucleotide, e.g., including complementary sequence 212', first complementary adapter 221', and second complementary adapter 222'. Similarly, duplex D3 may include a first target polynucleotide including sequence 213, first adapter 221, and second adapter 222, and a second target nucleotide that is complementary to the first target polynucleotide, e.g., including complementary sequence 212', first complementary adapter 221', and second complementary adapter 222'. Sequences 211, 212, and 213 may be different than one another, and it may be desired to determine those sequences using SBS. First adapters 221 may be complementary to capture primers 231 so as to be able to hybridize thereto under suitable conditions, and second adapters 222 may be complementary to orthogonal capture primers 232 so as to be able to hybridize thereto under suitable conditions. Although not specifically illustrated, each capture primer 231 or each orthogonal capture primer 232 may include a cleavable moiety such as 8-oxo-G.

Capture primers 231 may, for example, be P5 capture primers, and orthogonal capture primers 232 may, for example, be P7 capture primers. P5 capture primers, which are commercially available from Illumina, Inc. (San Diego, CA) have the sequence 5'-AATGATACGGCGACCACCGA-3' (SEQ ID NO: 1). P7 capture primers, which also are commercially available from Illumina, Inc., have the sequence 5'-CAAGCAGAAGACGGCATACGA-3' (SEQ ID NO: 2). First adapters 221 may be, for example, complementary P5 adapters (cP5) and second adapters 222 may be, for example, complementary P7 adapters (cP7). Complementary P5 adapters, which are commercially available from Illumina, Inc. (San Diego, CA), have the sequence 5'-TCGGTGGTCGCCGTATCATT-3' (SEQ ID NO: 3). Complementary P7 adapters, which are commercially available from Illumina, Inc. (San Diego, CA), may have the sequence 5'-TCGTATGCCGTCTTCTGCTTG-3' (SEQ ID NO: 4).

Before attempting to capture the target polynucleotides on substrate 200 for later amplification and sequencing, duplexes D1, D2, and D3 are melted in a manner such as illustrated in FIG. 2B so as to obtain single-stranded target polynucleotides having first adapters 221 that are available to hybridize to capture primers 231, and second adapters 222 that are available to hybridize to orthogonal capture primers 232. Such melting may be performed, for example, by changing the temperature and/or composition of the solution in which duplexes D1, D2, and D3 are disposed. For example, duplexes D1, D2, and D3 may be exposed to a sufficient amount of formamide in solution, e.g., about 1% to 100% formamide (% v/v), or about 5% to about 80% formamide (% v/v), or about 10% to about 50% formamide (% v/v), or about 1% to about 20% formamide (% v/v), to cause the duplexes to dissociate at the current solution temperature. Additionally, or alternatively, the temperature of the solution may be increased above the melting temperature (Tm) of the duplexes at the current solution composition. It will be appreciated that the particular Tm of a duplex may depend on the composition of the solution (e.g., salt (Na+) concentration and formamide concentration, if any), as well as the length and sequences of the polynucleotides in the duplex.

After the duplexes D1, D2, and D3 are melted such as described with reference to FIG. 2B, first adapters 221 may be available to hybridize to capture primers 231, and second adapters 222 may be available to hybridize to orthogonal capture primers 232. However, the solution and temperature conditions that caused such melting also may inhibit first adapters 221 from hybridizing to capture primers 231, and may inhibit second adapters 222 from hybridizing to orthogonal capture primers 232. So as to promote such hybridization and thus promote capture of the target polynucleotides on substrate 200, the temperature and/or composition of the solution in which the target polynucleotides are disposed again may be changed. For example, a sufficient amount of formamide may be removed from the solution at the current solution temperature. Additionally, or alternatively, the temperature of the solution may be decreased below the melting temperature (Tm) of duplexes between (a) first adapters 221 and capture primers 231 and (b) second adapters 222 and orthogonal capture primers 232, at the current solution composition.

In the nonlimiting example illustrated in FIG. 2C, this additional change in conditions, e.g., solution temperature and/or composition, facilitates hybridization between the second adapter 222 coupled to sequence 211 and one of capture primers 232; and hybridization between first adapter 221 coupled to sequence 213 and one of capture primers 231. However, this additional change in conditions also facilitates annealing between target polynucleotides in solution. For example, the first and second target polynucleotides respectively including sequences that are complementary to one another may reanneal with each other along their lengths, illustratively, such as sequences 212 and 212' that reanneal along their lengths to re-form duplex D2. Additionally, first and second target polynucleotides including sequences that are not complementary to one another may partially anneal with each other, e.g., at adapters 221 and 221' and at adapters 222 and 222', illustratively, such as non-complementary sequences 214 and 211' that anneal substantially only at their adapters to form duplex D4 in a manner such as illustrated in FIG. 2C. Target polynucleotides that anneal in solution to form duplexes, illustratively, the target polynucleotides including sequences 212 and 214 in the nonlimiting example shown in FIG. 2C, are unavailable to hybridize with capture primers 231 or orthogonal capture primers 232 and as such may not be captured, let alone amplified or sequenced.

In comparison, the present modified capture primers may be hybridized with the adapters of target polynucleotides under conditions at which annealing in solution substantially may not occur, e.g., at a salt concentration, formamide content, and/or temperature at which annealing in solution substantially may not occur. As such, target polynucleotides substantially may not anneal in such solution to form duplexes and therefore may remain available to hybridize with the present capture primers, following which they may be amplified and sequenced or otherwise used as desired. Additionally, the present modified capture primers may be hybridized with the adapters of target polynucleotides under conditions that inhibit any non-specific or non-productive hybridization of target polynucleotides to capture primers or to adapters in solution, and as such it may be expected that substantially all hybridization events will be productive and will lead to duplexes that may be sequenced.

FIGS. 3A-3H schematically illustrate example compositions and operations in an example process flow for capture and amplification of polynucleotides on a substrate using the present capture primers. Composition 3000 illustrated in FIG. 3A includes substrate 300 having capture primers 331 and orthogonal capture primers 332 coupled thereto, as well as a fluid (solution) containing target polynucleotides, e.g., polynucleotides that it is intended to capture, amplify, and sequence using sequencing-by-synthesis (SBS). The target polynucleotides may include or may be provided in the form of duplexes (illustratively, duplexes D5, D6, and D7) between target polynucleotides having sequences that are complementary to one another. For example, in a manner similar to that described with reference to FIG. 2A, duplex D5 may include a first target polynucleotide including sequence 311, first adapter 321, and second adapter 322, and a second target nucleotide that is complementary to the first target polynucleotide, e.g., including complementary sequence 311', first complementary adapter 321', and second complementary adapter 322'. Similarly, duplex D6 may include a first target polynucleotide including sequence 312, first adapter 321, and second adapter 322, and a second target nucleotide that is complementary to the first target polynucleotide, e.g., including complementary sequence 312', first complementary adapter 321', and second complementary adapter 322'. Similarly, duplex D7 may include a first target polynucleotide including sequence 313, first adapter 321, and second adapter 322, and a second target nucleotide that is complementary to the first target polynucleotide, e.g., including complementary sequence 312', first complementary adapter 321', and second complementary adapter 322'. Sequences 311, 312, and 313 may be different than one another, and it may be desired to determine those sequences using SBS. First adapters 321 may be complementary to capture primers 331 so as to be able to hybridize under suitable conditions, and second adapters 322 may be complementary to modified orthogonal capture primers 332 so as to be able to hybridize thereto under suitable conditions.

Each of capture primers 331 may include a plurality of nucleic acids that increase the Tm of duplexes between capture primers 331 and first adapters 321 as compared to the Tm of duplexes between first adapters 321 and complementary first adapters 321'. For example, the modified nucleic acids of capture primers 331 may include locked nucleic acid (LNA), peptide nucleic acid (PNA), or super T, each of which may be expected to increase the Tm of duplexes between capture primers 331 and first adapters 321 as compared to the Tm of duplexes between first adapters 321 and complementary first adapters 321'. Capture primers 331 further may include DNA. The modified nucleic acids and the DNA may be distributed between a 5' end and a 3' end of the capture primers. For example, the sequences of capture primers 331 may include one or more DNA molecules, followed by one or more modified nucleic acids, followed by one or more DNA molecules, followed by one or more modified nucleic acids, and so on. Alternatively, the modified nucleic acids may be disposed at a 5' end of the capture primers and the DNA is disposed at a 3' end of the capture primers, e.g., in a manner such as described below with reference to FIG. 4. Although not specifically illustrated, each capture primer 331 also may include a cleavable moiety such as 8-oxo-G.

Similarly, each of orthogonal capture primers 332 may include a plurality of modified nucleic acids that increase the Tm of duplexes between orthogonal capture primers 332 and second adapters 322 as compared to the Tm of duplexes between second adapters 322 and complementary second adapters 322'. For example, the modified nucleic acids of orthogonal capture primers 332 may include locked nucleic acid (LNA), peptide nucleic acid (PNA), or super T, each of which may be expected to increase the Tm of duplexes between orthogonal capture primers 332 and second adapters 322 as compared to the Tm of duplexes between second adapters 322 and complementary second adapters 322'. Orthogonal capture primers 332 further may include deoxyribonucleic acid (DNA). The modified nucleic acids and the DNA may be distributed between a 5' end and a 3' end of the orthogonal capture primers. For example, the sequences of orthogonal capture primers 332 may include one or more DNA molecules, followed by one or more modified nucleic acids, followed by one or more DNA molecules, followed by one or more modified nucleic acids, and so on. Alternatively, the modified nucleic acids may be disposed at a 5' end of the capture primers and the DNA is disposed at a 3' end of the capture primers, e.g., in a manner such as described below with reference to FIG. 4. Although not specifically illustrated, each orthogonal capture primer 332 also may include a cleavable moiety such as 8-oxo-G.

Note that the modified nucleic acids of capture primers 331 may be, but need not necessarily be, the same type of modified nucleic acids of orthogonal capture primers 332. Illustratively, capture primers 331 and orthogonal capture primers 332 may include LNA; capture primers 331 and orthogonal capture primers 332 may include PNA; or capture primers 331 and orthogonal capture primers 332 may include super T. Alternatively, capture primers 331 may include LNA while orthogonal capture primers 332 may include PNA or super T; capture primers 331 may include PNA while orthogonal capture primers 332 may include LNA or super T; or capture primers 331 may include super T while orthogonal capture primers 332 may include LNA or PNA. In still other examples, orthogonal capture primers 332 may include LNA while capture primers 331 may include PNA or super T; orthogonal capture primers 332 may include PNA while capture primers 331 may include LNA or super T; or orthogonal capture primers 332 may include super T while capture primers 331 may include LNA or PNA.

LNA closely mimics DNA with the only change being a linker that connects the 2' and 4' carbons. PNAs are structured similarly to a polypeptide, with a carboxylic acid group and an amino group. Super T includes a modified thymidine base with a butyne group. In the case of LNA and super T base modifications, increased rigidity of the molecular structure and stronger base stacking may increase the binding energy of the duplex interaction (321-331 or 322-332) as compared to DNA/DNA duplexes (321-321' or 322-322'). On the other hand, the melting point of duplexes containing un-charged PNA (321-331 or 322-332) may be increased compared DNA/DNA duplexes (321-321' or 322-322') due to reduced electrostatic repulsion. When capture primer sequences are modified to include such modified nucleic acids, the melting point between the surface/solution duplex (321-331 or 322-332) can be made significantly higher than the melting point of the solution/solution DNA duplex (321-321' or 322-322'). This allows for the target polynucleotides 311, 312, 313 to be seeded at a set of conditions (e.g., salt concentration, formamide concentration, and temperature) that does not allow for reannealing of adapters in solution. As such, the target polynucleotides 311, 312, 313 may be seeded with substantially no loss from adapter reannealing such as described with reference to FIG. 2C.

Figure 3A:
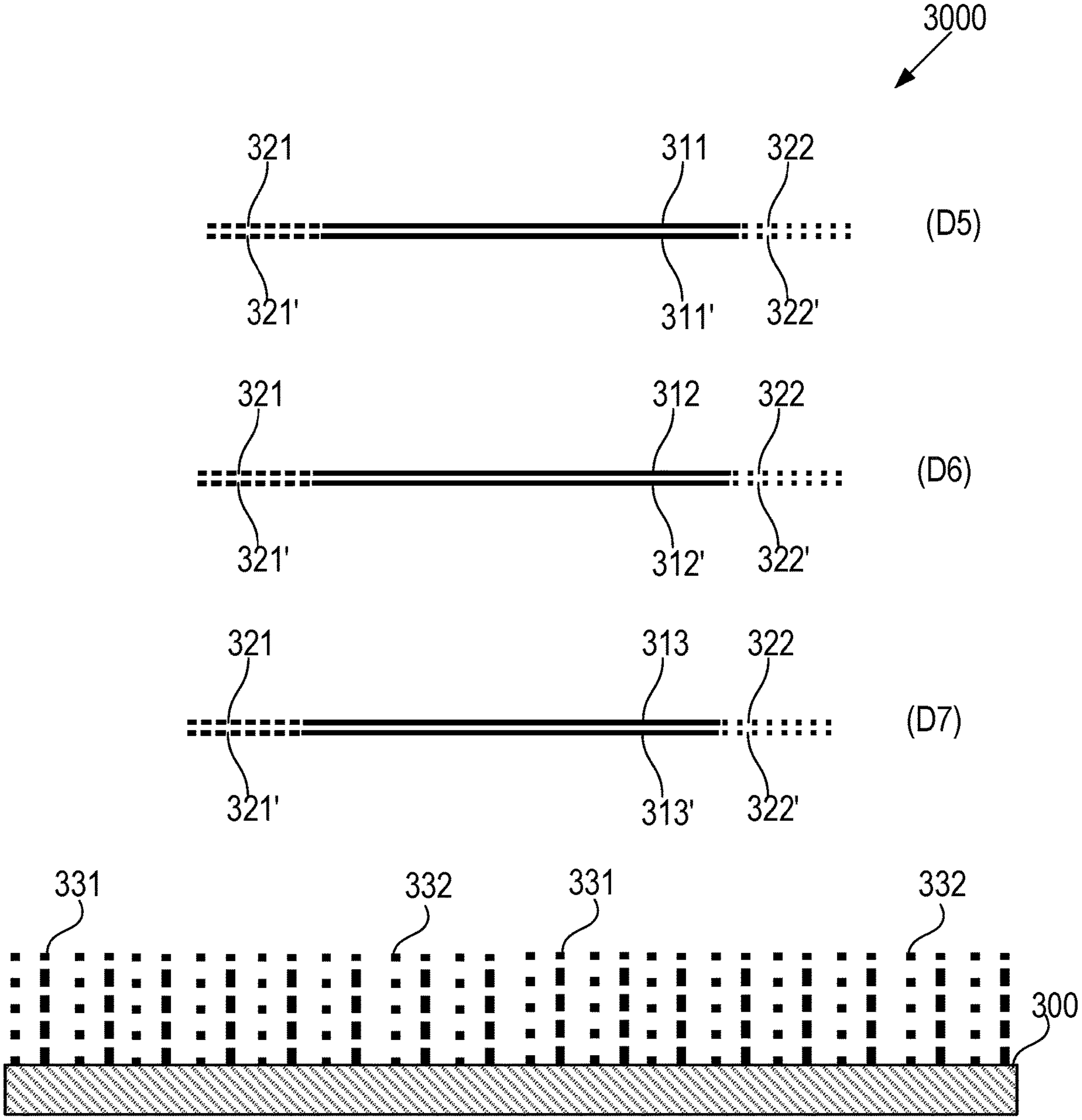
FIGS. 3A-3H schematically illustrate example compositions and operations in an example process flow for capture and amplification of polynucleotides on a substrate using the present capture primers.
Figure 3B:
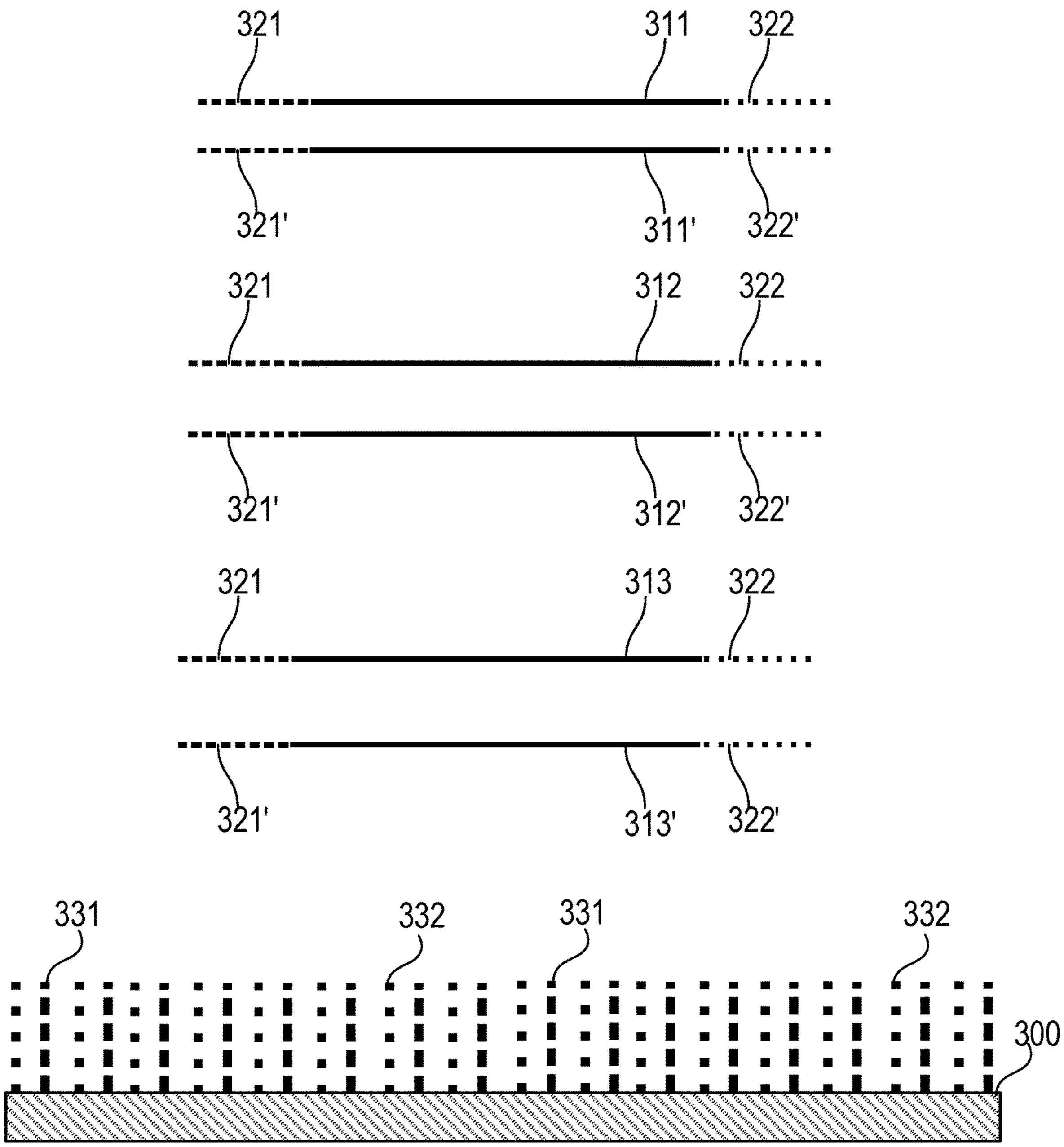

Before attempting to capture the target polynucleotides on substrate 300 for later amplification and sequencing, duplexes D5, D6, and D7 are melted in a manner such as illustrated in FIG. 3B so as to obtain single-stranded target polynucleotides having first adapters 321 that are available to hybridize to capture primers 331, and second adapters 322 that are available to hybridize to orthogonal capture primers 332. In a manner similar to that described with reference to FIG. 2B, such melting may be performed, for example, by changing the temperature and/or composition of the solution in which duplexes D5, D6, and D7 are disposed. For example, duplexes D5, D6, and D7 may be exposed to a sufficient amount of formamide in solution, e.g., about 1% to 100% formamide (% v/v)), or about 5% to about 80% formamide (% v/v), or about 10% to about 50% formamide (% v/v), or about 1% to about 20% formamide (% v/v), to cause the duplexes to dissociate at the current solution temperature. Additionally, or alternatively, the temperature of the solution may be increased above the melting temperature (Tm) of the duplexes at the current solution composition. It will be appreciated that the particular Tm of a duplex may depend on the composition of the solution (e.g., salt (Na+) concentration and formamide concentration, if any), as well as the length and sequences of the polynucleotides in the duplex.

Figure 3C:
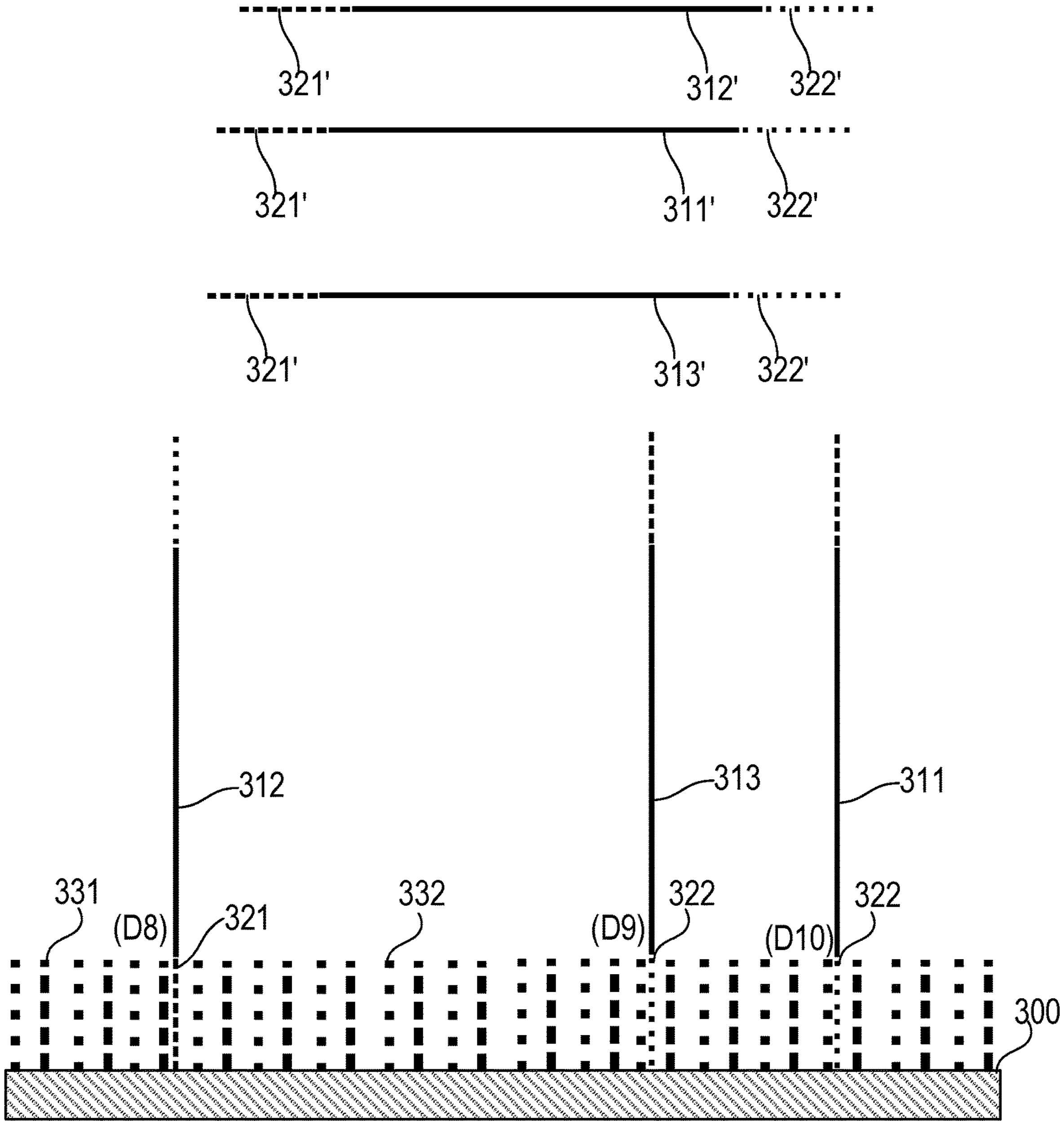

After the duplexes D5, D6, and D7 are melted such as described with reference to FIG. 3B, first adapters 321 may hybridize to capture primers 331, and second adapters 322 may hybridize to orthogonal capture primers 332 at the same conditions that were used to melt duplexes D5, D6, and D7, in a manner such as illustrated in FIG. 3C. That is, the solution and temperature conditions that caused such melting may not inhibit first adapters 321 from hybridizing to capture primers 331, and may not inhibit second adapters 322 from hybridizing to orthogonal capture primers 332. Instead, such conditions may inhibit any annealing between adapters 321 and complementary adapters 321' and any reannealing between adapters 322 and complementary adapters 322' and thus may inhibit formation of any duplexes such as described with reference to FIG. 2C. As such, each of the target polynucleotides may remain available for capture, and may be captured on substrate, without necessarily changing the conditions that were used to melt duplexes D5, D6, and D7, e.g., without necessarily reducing the concentration of formamide and without necessarily decreasing the solution temperature.

In the nonlimiting example illustrated in FIG. 3C, at conditions that inhibit annealing between target polynucleotides in solution, the first adapters 321 of some of the target polynucleotides are hybridized to respective ones of the capture primers 331 to form first duplexes, and the second adapters 322 of some of the target polynucleotides are hybridized to respective ones of the orthogonal capture primers 332 to form second duplexes. The first and second duplexes each may have a melting temperature (Tm) that is greater than a Tm of third duplexes that would be formed by hybridization of the second target polynucleotides to the respective ones of the first target polynucleotides to which the second target polynucleotides are complementary. Illustratively, first adapter 321 coupled to sequence 312 is hybridized to one of capture primers 331 to form duplex D8; second adapter 322 coupled to sequence 311 is hybridized to one of orthogonal capture primers 332 to form duplex D9; and second adapter 322 coupled to sequence 313 is hybridized to one of orthogonal capture primers 332 to form duplex D10.

The Tins of duplexes between first adapters 321 and capture primers 331 may be greater than the Tins of duplexes between first adapters 321 and complementary first adapters 321', e.g., may exceed the Tins of duplexes between first adapters 321 and complementary first adapters 321' by at least about 5° C., by at least about 10° C., by at least about 15° C., by at least about 20° C., or by at least about 25° C. Similarly, the Tins of duplexes between second adapters 322 and orthogonal capture primers 332 may be greater than the Tins of duplexes between second adapters 322 and complementary second adapters 322', e.g., may exceed the Tins of duplexes between first adapters 321 and complementary first adapters 321' by at least about 5° C., by at least about 10° C., by at least about 15° C., by at least about 20° C., or by at least about 25° C. As such, the target polynucleotides suitably may be captured on substrate 300 at a temperature that is below the Tms of duplexes between first adapters 321 and capture primers 331 and below the Tms of duplexes between second adapters 322 and orthogonal capture primers 332, and that is above the Tins of duplexes between first adapters 321 and complementary first adapters 321' and that is above the Tms of duplexes between second adapters 322 and complementary second adapters 322'.

Illustratively, the Tms of duplexes D8, D9, and D10 illustrated in FIG. 3C may be greater than the Tms of any of duplexes D1, D2, D3, and D4 described with reference to FIGS. 2A and 2C. For example, duplexes D8, D9, and D10 each may have a melting temperature (Tm) that is between about 80° C. and about 110° C., e.g., between about 85° C. and about 105° C., or between about 90° C. and about 100° C. In comparison, the Tins of duplexes D1, D2, D3, and D4 may be below about 80° C., e.g., below about 75° C., below about 70° C., below about 65° C., or below about 60° C. As a result of the significantly different Tins of duplexes between adapters and the surface primers as compared to the Tms of duplexes between adapters in solution, substantially none of the second target polynucleotides are hybridized in solution to any of the first target polynucleotides. As such, duplexes D8, D9, and D10 readily may form at certain conditions under which duplexes D1, D2, D3, and D4 may not form. The duplexes may form on the surface of substrate 300 at different locations, e.g., in accordance with the Poisson distribution. Although not specifically illustrated, it will be appreciated that substrate 300 may be patterned, e.g., so as to define different regions within which a duplex respectively may form, and within which clusters subsequently may be formed using amplification. Additionally, although the examples described with reference to FIGS. 3A-3H are illustrated so as to suggest the use of flat substrates, it should be apparent that more complex substrates may be used, e.g., that include wells that respectively are seeded by target polynucleotides and within which substantially monoclonal clusters may be formed.

Figure 3D:
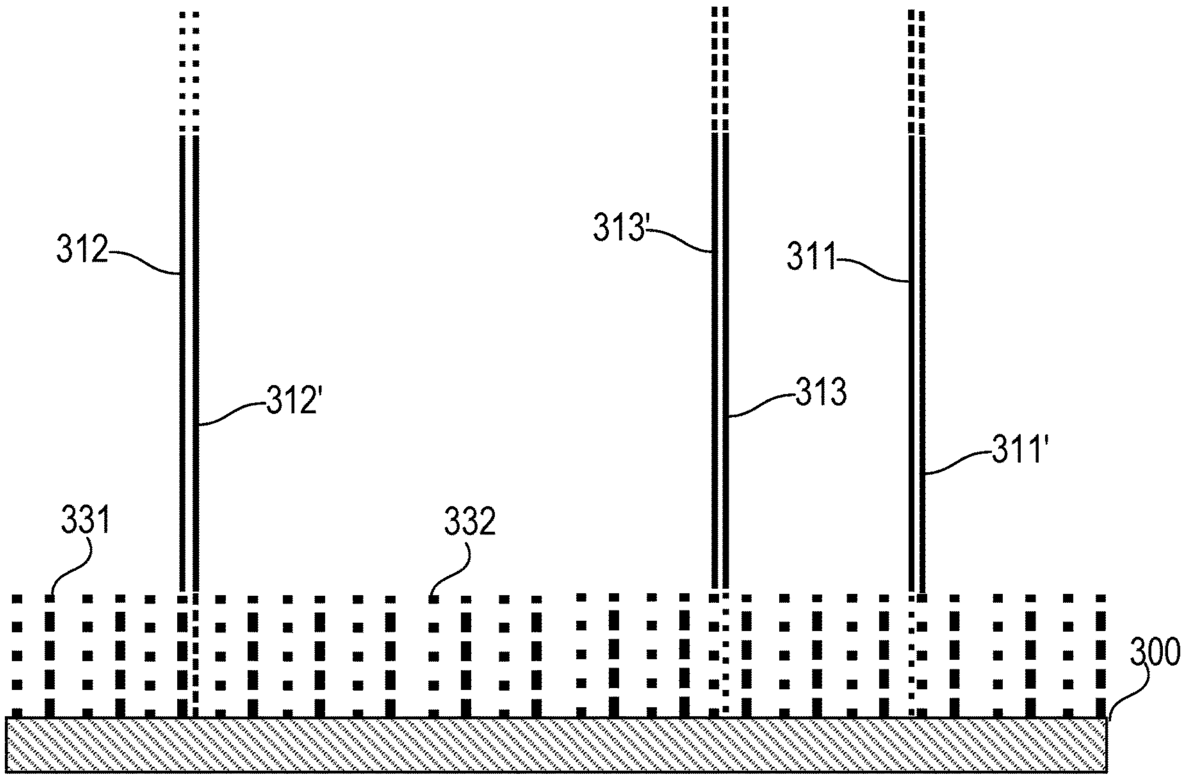
Figure 3E:
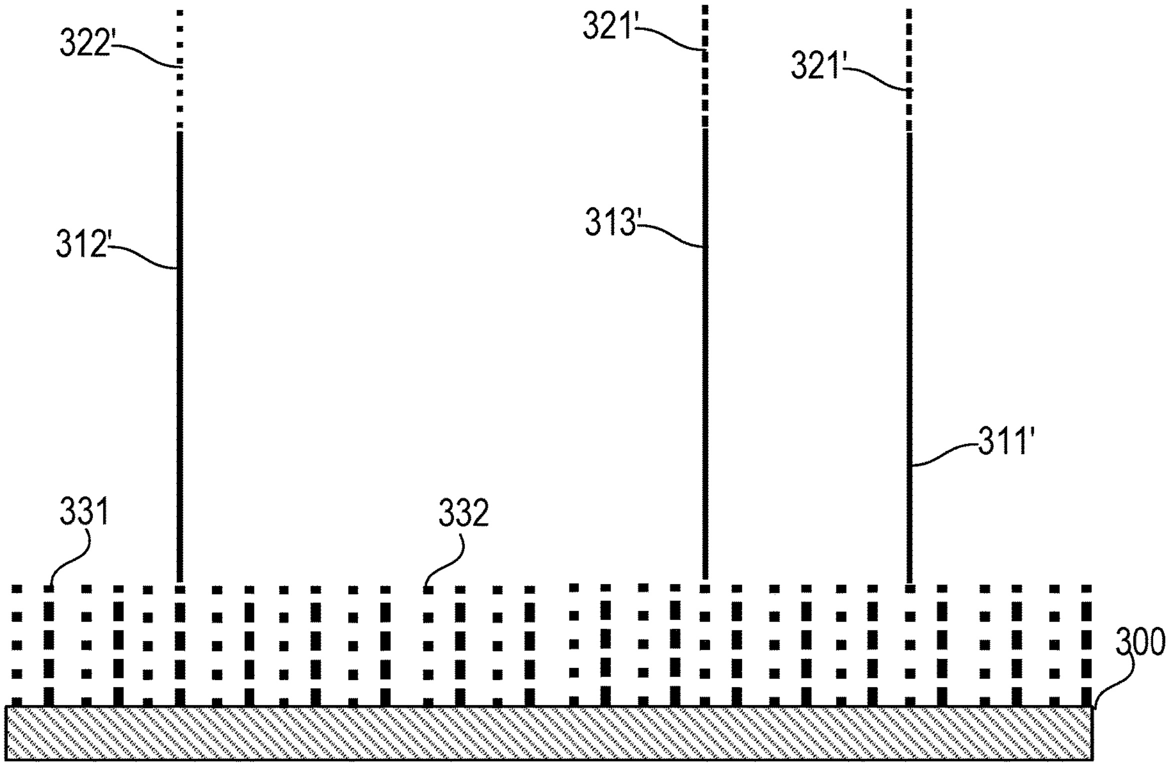

As illustrated in FIG. 3D, after the initial hybridizations described with reference to FIG. 3C, each of the target polynucleotides 311, 312, 313 may be amplified so as to form respective amplicons 311', 312', and 313', respectively. Following such amplification, the target polynucleotides 311, 312, 313 may be dehybridized in a manner such as illustrated in FIG. 3E, while amplicons 311', 312', and 313' remain covalently bound to substrate 300. Note that such dehybridization need not necessarily be performed. For example, instead of dehybridizing target polynucleotides 311, 312, 313, such polynucleotides may remain hybridized to the substrate and may be further amplified using a strand invasion process such as known in the art and may be referred to as ExAmp.

Figure 3F:
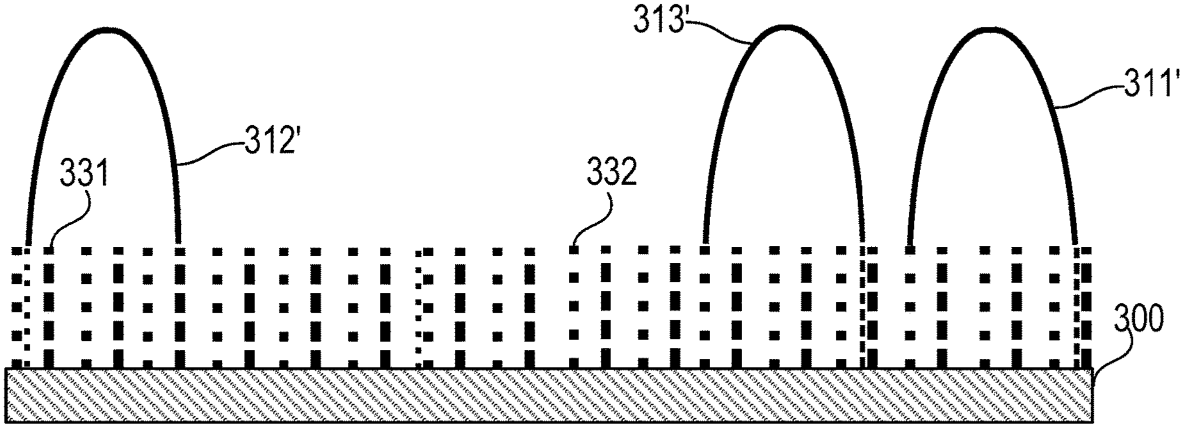

As illustrated in FIG. 3F, after the initial amplifications described with reference to FIGS. 3D-3E, the resulting amplicons may bend so as potentially to hybridize to other capture primers or orthogonal capture primers on substrate 300. For example, complementary first adapter 321' of amplicon 311' may hybridize to one of capture primers 331; complementary second adapter 322' of amplicon 312' may hybridize to one of orthogonal capture primers 332; and complementary first adapter 321' of amplicon 313' may hybridize to one of capture primers 331. The duplexes between the amplicons' adapters and respective capture primers or orthogonal capture primers may have similar or the same Tms as duplexes D8, D9, and D10, and thus may remain hybridized so as to promote further amplification of the target polynucleotides.

Figure 3G:
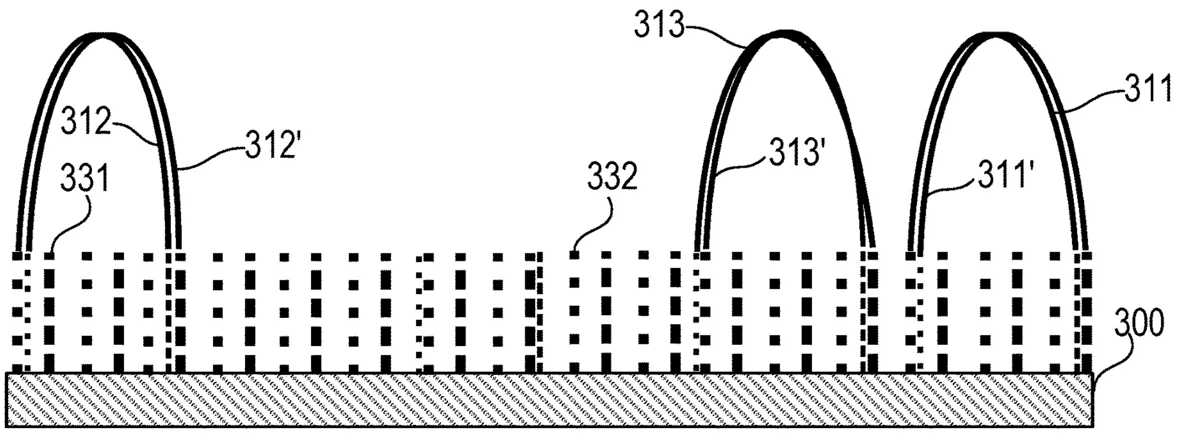
Figure 3H:
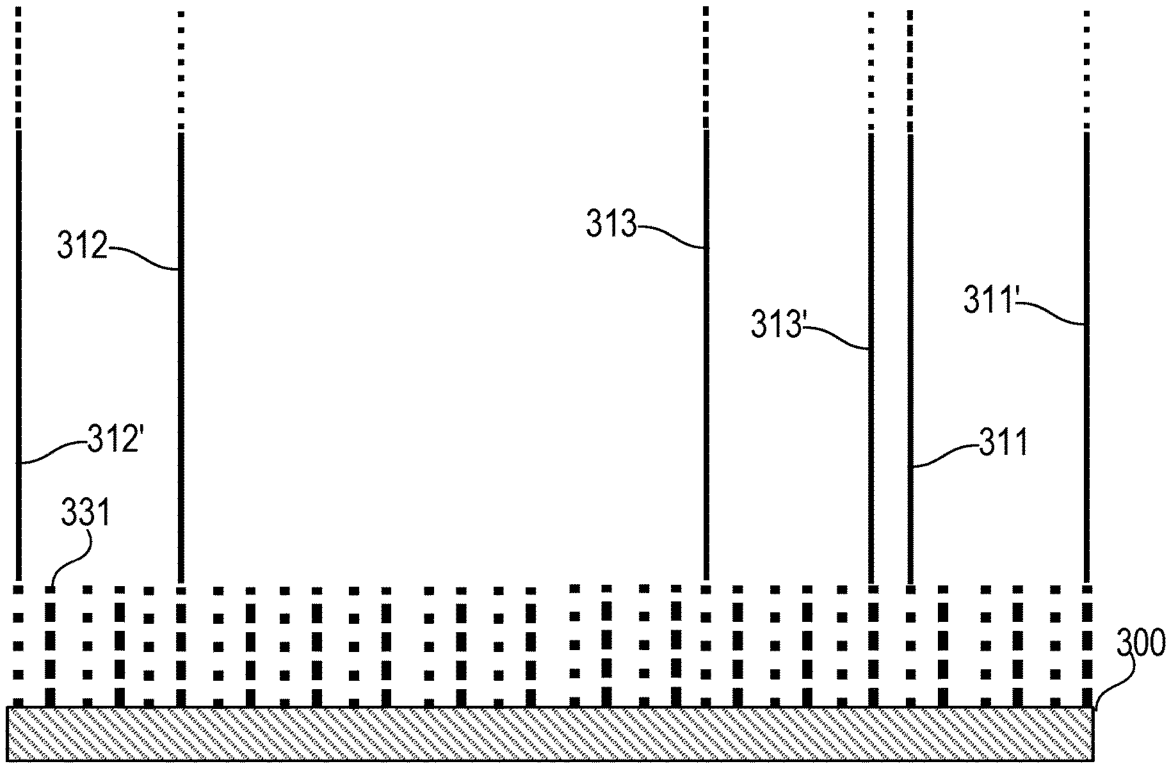

FIG. 3G illustrates the composition of FIG. 3F following another amplification operation. It may be seen that the composition includes an additional amplicon 311 of amplicon 311'; an additional amplicon 312 of amplicon 312'; and an additional amplicon 313 of amplicon 313'. Such additional amplicons may be hybridized to the amplicons from which they were generated. The solution may be increased so as to dehybridize the amplicon's adapters from the capture primers or orthogonal capture primers in a manner such as illustrated in FIG. 3H. The amplification operation may be repeated any suitable number of times so as to generate further amplicons of amplicons 311, 311', 312, 312', 313, and 313'. Amplification operations may be formed any suitable number of times so as to substantially fill respective substrate regions (not specifically illustrated) with substantially monoclonal clusters, e.g., with amplicons of target polynucleotide 311, 312, or 313, respectively. For example, amplicons within each of the substrate regions each may include at least about 60% amplicons of one selected target polynucleotide, or at least about 70% amplicons of one selected target polynucleotide, or at least about 80% amplicons of one selected target polynucleotide, or at least about 90% amplicons of one selected target polynucleotide, or at least about 95% amplicons of one selected target polynucleotide, or at least about 98% amplicons of one selected target polynucleotide, or at least about 99% amplicons of one selected target polynucleotide, or about 100% amplicons of one selected target polynucleotide.

As noted above, in some examples, certain capture primers and orthogonal capture primers may include non-nucleotide moieties. Such non-nucleotide moieties may include, but are not limited to, excision moieties via which a portion of the capture primers selectively may be removed. The excision moieties may be located at any suitable position along the length of any suitable primer(s) and may be, but need not necessarily be, the same type of excision moiety as one another. Following a desired number of additional amplification operations such as described with reference to FIGS. 3E-3H, portions of capture primers 331 or orthogonal capture primers 332 may be removed by reacting suitable enzyme(s) or reagent(s) with the excision moieties.

Figure 4:
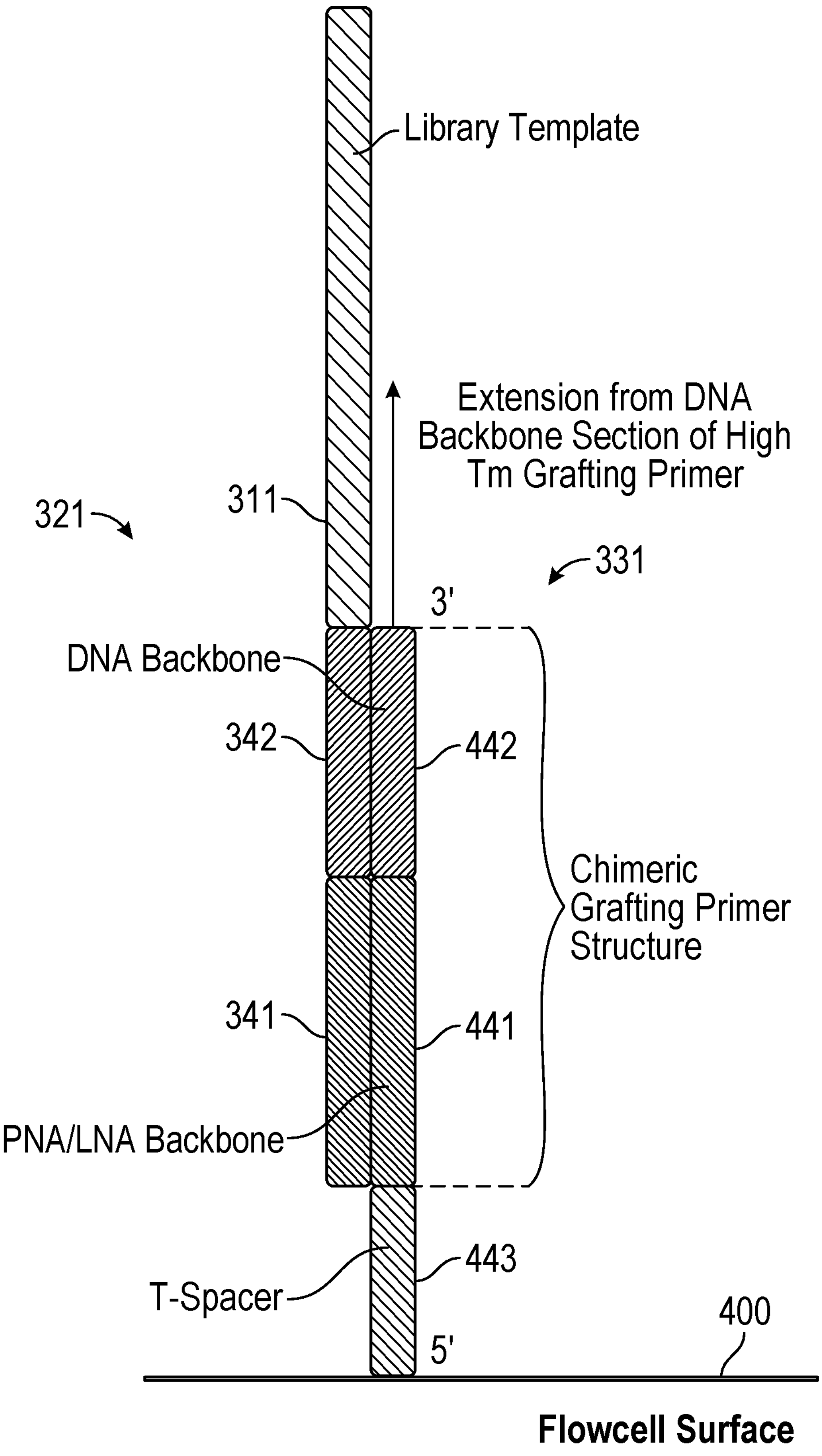
FIG. 4 schematically illustrates an example duplex between a polynucleotide and one of the present capture primers, according to some examples.

The present capture primers and orthogonal capture primers may include any suitable number, type, and arrangement of modified nucleic acids that sufficiently increases the Tins of duplexes between those capture primers or orthogonal capture primers, and adapters of the target polynucleotides. FIG. 4 schematically illustrates an example duplex between a polynucleotide and one of the present capture primers, according to some examples. In the nonlimiting example illustrated in FIG. 4, modified nucleic acids 441 (such as PNA or LNA) are disposed at a 5' end of capture primer 331 and DNA 442 is disposed at a 3' end of the capture primer. An optional T-spacer 443 is disposed between DNA 442 and the surface of substrate 400 (e.g., flowcell). Together, modified nucleic acids 441 and DNA 442 may be considered to provide a "chimeric" grafting primer structure. The target polynucleotide may include library template 311 coupled to adapter 321 which includes a first subsequence 341 that is complementary to the sequence of modified nucleic acids 441, and a second subsequence 342 that is complementary to the sequence of DNA 442. Alternatively, the modified nucleic acids (such as PNA, LNA, or super T) and the DNA are distributed between a 5' end and a 3' end of the capture primers in a manner such as described further above. Orthogonal capture primers 332 may be configured similarly as capture primer 331 illustrated in FIG. 4, e.g., may include a chimeric grafting primer structure, but with different sequences. Alternatively, the modified nucleic acids (such as PNA, LNA, or super T) and the DNA may be distributed between a 5' end and a 3' end of the orthogonal capture primers in a manner such as described further above.

In some examples, each of the capture primers 331 may include between about five and about twenty of the modified nucleic acids, and each of the orthogonal capture primers 332 may include between about five and about twenty of the modified nucleic acids. However, it will be appreciated that the number of modified nucleic acids suitably may be adjusted to obtain an appropriate Tm for use in conditions that inhibit duplex formation in solution while allowing duplex formation at the substrate surface, and that the capture primers and orthogonal capture primers need not include the same number, type, or distribution of modified nucleic acids as each other. Illustratively, each of the capture primers may include at least about nine of the modified nucleic acids, and each of the orthogonal capture primers may include at least about nine of the modified nucleic acids; or each of the capture primers may include at least about twelve of the modified nucleic acids, and each of the orthogonal capture primers may include at least about twelve of the modified nucleic acids; or each of the capture primers may include at least about fifteen of the modified nucleic acids, and each of the orthogonal capture primers may include at least about fifteen of the modified nucleic acids.

Note that although capture primers 331 and orthogonal capture primers 332 include modified nucleic acids, they otherwise may have similar or the same sequences as capture primers 231 and 232. That is, capture primers 331 may be modified P5 capture primers, and wherein the orthogonal capture primers are modified P7 capture primers. For example, capture primers 331 may be or include P5 primers having the sequence provided elsewhere herein, in which at least some of the P5 DNA bases are replaced with their PNA, LNA, or super T analogues. Additionally, or alternatively, orthogonal capture primers 332 may be or include P7 primers having the sequence provided elsewhere herein, in which at least some of the P7 DNA bases are replaced with their PNA, LNA, or super T analogues. Nonlimiting examples of chimeric P5 and P7 sequences including varying lengths of LNA, the calculated Tm for a duplex between the chimeric P5 or P7 sequence and their respective adapter cP5 or cP7 (750 mM Na+) are provided in Table 1 below in which bolded text indicates LNA, and unbolded text indicates DNA. The commercially available P5 and P7 sequences, and the calculated Tm for a duplex between the P5 or P7 sequence and their respective adapter cP5 or cP7, are provided for reference.

TABLE 1

High Tm DNA/LNA chimeric P5/P7

| Type | Sequence | Tm (°C) |
|---|---|---|
| Standard P5 (SEQ ID NO: 5) | TTTTTT AATGA TACGG CGACC ACCGA GAUCT ACAC | 78.1 |
| LNA-mod. P5 (SEQ ID NO: 6) | TTTTTT **AATGA TACGG CGACC** ACCGA GAUCT ACAC | 99.1 |
| LNA-mod. P5 (SEQ ID NO: 7) | TTTTTT **AATGA TACGG CG**ACC ACCGA GAUCT ACAC | 94.1 |
| LNA-mod. P5 (SEQ ID NO: 8) | TTTTTT **AATGA TACG**G CGACC ACCGA GAUCT ACAC | 89.1 |
| Standard P7 (SEQ ID NO: 9) | TTTTTT CAAGC AGAAG ACGGC ATAC(8-oxoG) AGAT | 72.1 |
| LNA-mod. P7 (SEQ ID NO: 10) | TTTTTT **CAAGC AGAAG ACGGC** ATAC(8-oxoG) AGAT | 93.2 |
| LNA-mod. P7 (SEQ ID NO: 11) | TTTTTT **CAAGC AGAAG AC**GGC ATAC(8-oxoG) AGAT | 89.1 |
| LNA-mod. P7 (SEQ ID NO: 12) | TTTTTT **CAAGC AGAA**G ACGGC ATAC(8-oxoG) AGAT | 84.7 |

From the examples provided in Table 1, it may be understood that for the P5 sequence, replacing fifteen DNA bases with LNA may increase the Tm of a duplex between that sequence and the cP5 adapter by about 21° C.; replacing twelve DNA bases with LNA may increase the Tm of a duplex between that sequence and the cP5 adapter by about 16° C.; and replacing nine DNA bases with LNA may increase the Tm of a duplex between that sequence and the cP5 adapter by about 11° C. Additionally, from the examples provided in Table 1, it may be understood that for the P7 sequence, replacing fifteen DNA bases with LNA may increase the Tm of a duplex between that sequence and the cP7 adapter by about 21° C.; replacing twelve DNA bases with LNA may increase the Tm of a duplex between that sequence and the cP7 adapter by about 17° C.; and replacing nine DNA bases with LNA may increase the Tm of a duplex between that sequence and the cP7 adapter by about 12° C. It will be appreciated that the number of modified nucleic acids in any sequence in order to provide any suitable Tm for use in a capture primer or orthogonal capture primer such as provided herein.

One consideration for implementing the present modified capture primers is that such primers be compatible with suitable enzymes, such as recombinases, single-stranded binding proteins, and polymerases, as may be used for cluster generation and sequencing. Chimera structures including PNA or LNA such as described with reference to FIG. 4 are expected to be compatible with such enzymes in a manner similar to that described in the following references, the entire contents of which are incorporated by reference herein: Levin et al., "Position-dependent effects of locked nucleic acid (LNA) on DNA sequencing and PCR primers," Nucleic Acids Research 34(20): e142, 11 pages (2006); and Misra et al., "Polyamide nucleic acid-DNA chimera lacking the phosphate backbone are novel primers for polymerase reaction catalyzed by DNA polymerases," Biochemistry 37: 1917-1925 (1998). Further information about LNA may be found in Braasch et al., "Locked nucleic acid (LNA): fine-tuning the recognition of DNA and RNA," Chemistry & Biology 8: 1-7 (2001), the entire contents of which are incorporated by reference herein. Providing DNA at the 3' end of a chimera structure such as described with reference to FIG. 4 may help to maintain expected enzyme activity by locating the unmodified DNA bases at positions with which the enzymes are likely to interact, while providing the modified nucleic acids at the 5' end of the chimera structure may enhance the strength of binding to an adapter.

Figure 5A:
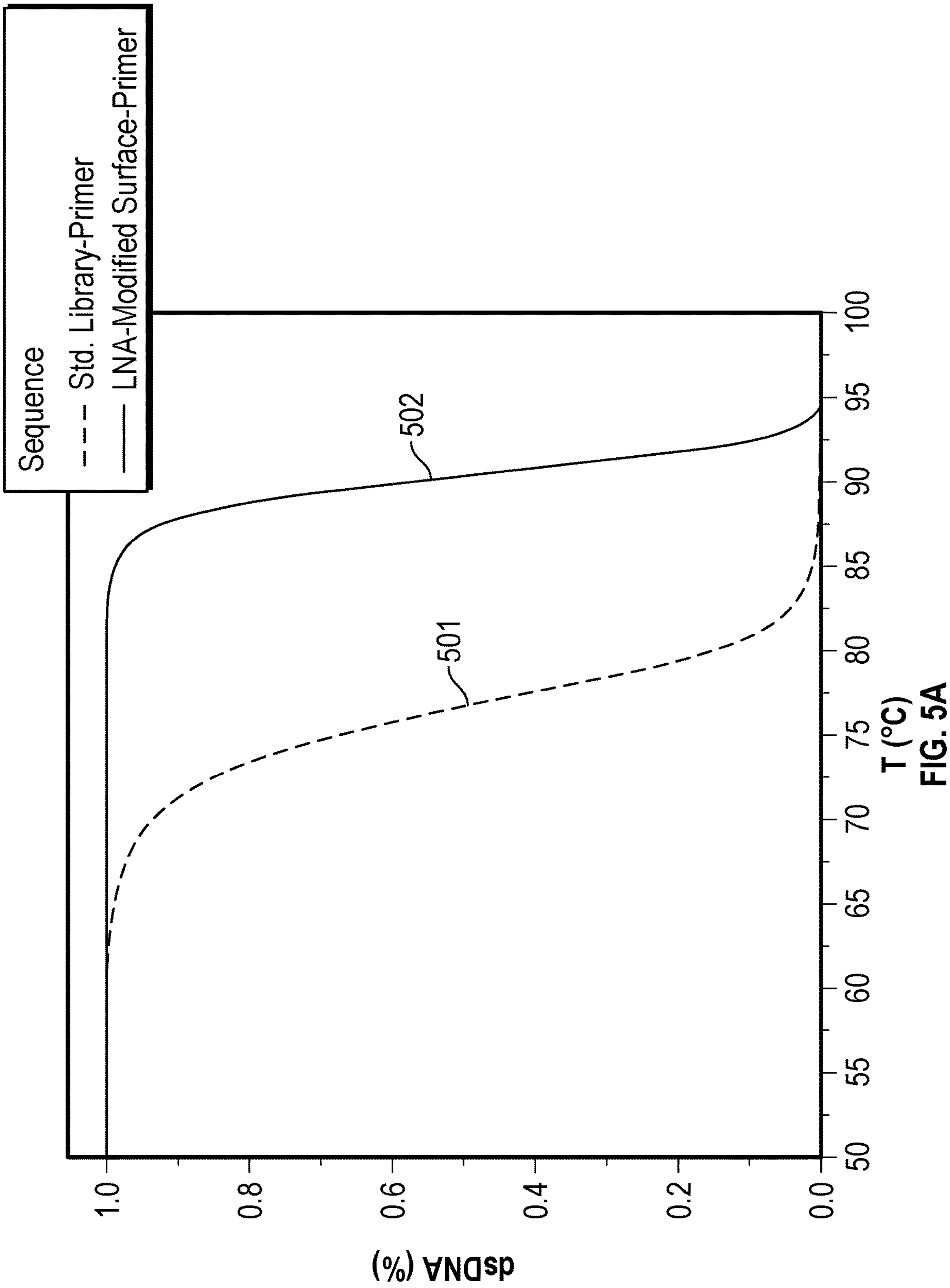
FIGS. 5A-5C are plots illustrating example effects of conditions on the capture of polynucleotides by the present capture primers.
Figure 5B:
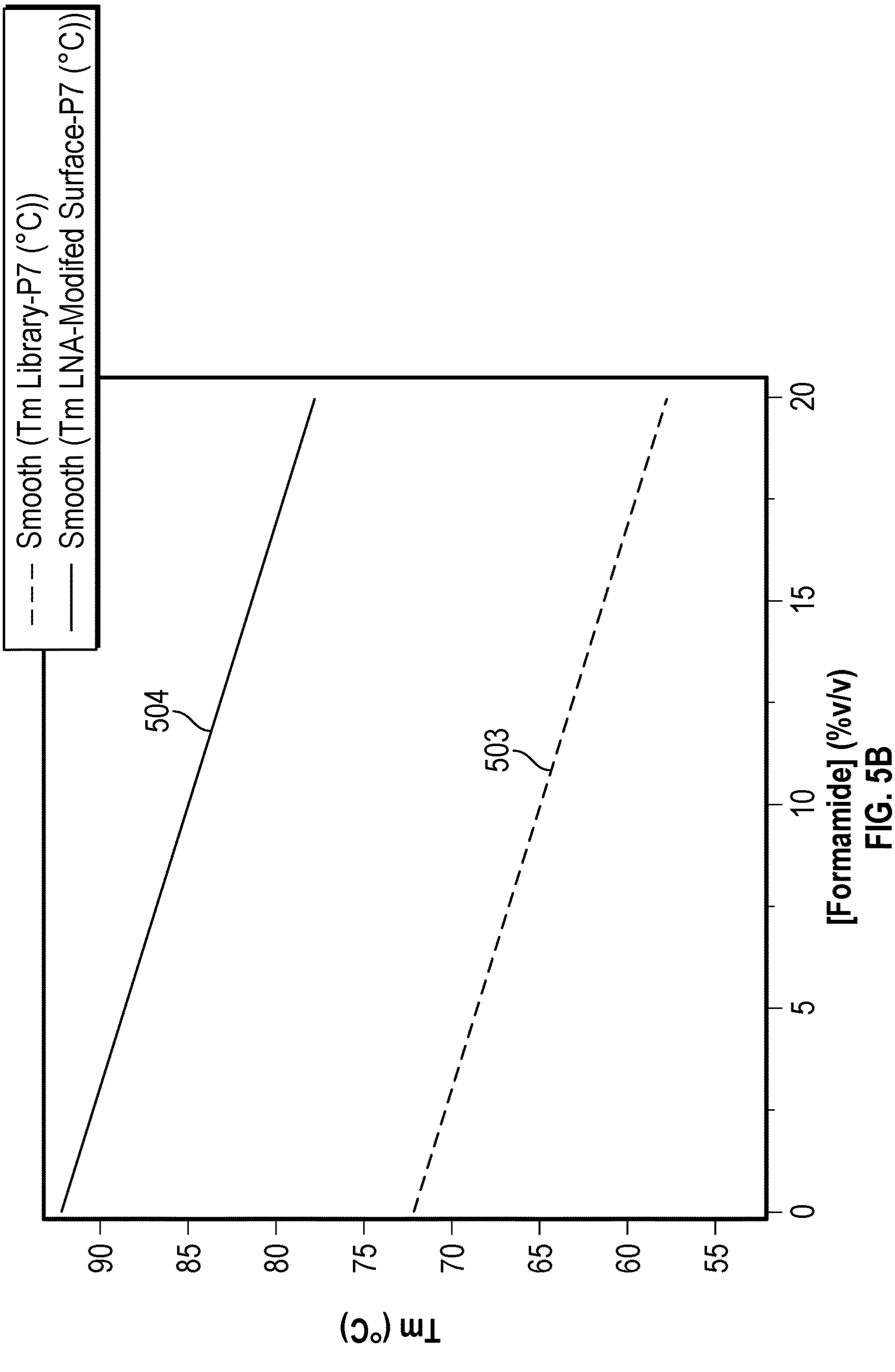
Figure 5C:
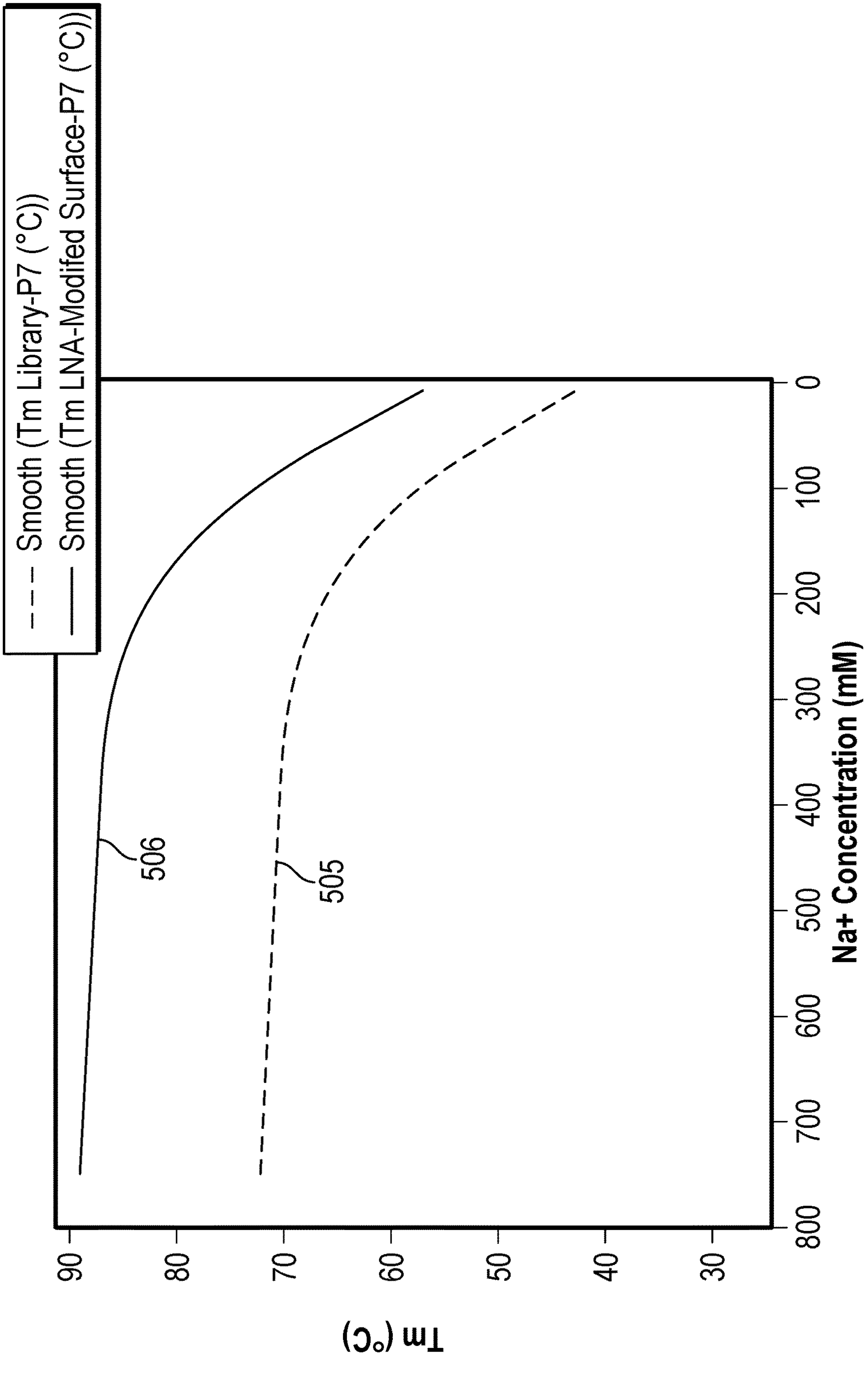

Additionally, as noted elsewhere herein and as will be appreciated by those skilled in the art, the Tm of any given duplex may vary based on the composition of the solution in which that duplex is disposed. For example, adding formamide to the solution may decrease the Tm of a given duplex, while adding salt to the solution may increase the Tm of a given duplex. As such, the example Tins provided herein (and differences between Tms.) are purely illustrative and may vary based on the particular composition of the solution in which the duplexes are disposed. FIGS. 5A-5C are plots illustrating example effects of conditions on the capture of polynucleotides by the present capture primers. In the nonlimiting example shown in FIG. 5A, the percent of double-stranded DNA (dsDNA) is shown as a function of temperature for duplexes formed by hybridization between cP7 and the P7 standard library capture primers (curve 501) and for duplexes formed by hybridization between cP7 and LNA-modified P7 capture primers (curve 502), in a solution including 0% v/v formamide and 750 mM Na+. The LNA-modified P7 capture primers had the sequence CAAGC AGAAG ACGGC ATAC(8-oxoG) AGAT (SEQ ID NO: 13) in which bolded text indicates LNA, and were modeled to have a 20° C. Tm when duplexed with cP7.

In FIG. 5A, it may be seen that a temperature of about 77° C. corresponds to the Tm of duplexes formed by hybridization between cP7 and the P7 standard library capture primers (curve 501), while a temperature of about 91° C. corresponds to the Tm of duplexes formed by hybridization between cP7 and LNA-modified P7 capture primers (curve 502). At temperatures above about 85° C., curve 501 shows that the percent dsDNA becomes insignificant (e.g., less than 1%) for duplexes formed by hybridization between cP7 and the P7 standard library capture primers. Additionally, at temperatures below about 90° C., curve 501 shows that the percent dsDNA is approximately 100% for duplexes formed by hybridization between cP7 and LNA-modified P7 capture primers. Accordingly, from FIG. 5A it may be understood that at a temperature of about 85° C.-90° C., hybridization between cP7 and the P7 standard library capture primers may be substantially completely inhibited, while hybridization between cP7 and LNA-modified P7 capture primers forms highly stable duplexes. As such, within this temperature range, template polynucleotides may be captured from solution with high efficiency and with substantially no competition from solution-based annealing processes such as described with reference to FIG. 2C. It will be appreciated that the particular temperature range suitable for performing such operations may vary depending on the particular composition of the solution. It may be expected that any other capture primer and adapter sequences will exhibit a similar dependence of duplex formation upon temperature.

For example, in the nonlimiting example shown in FIG. 5B, the Tms for duplexes formed by hybridization between cP7 and the P7 standard library capture primers (curve 503) and for duplexes formed by hybridization between cP7 and LNA-modified P7 capture primers (curve 504) are shown as a function of formamide concentration (% v/v), for a salt concentration of 750 mM Na+. Similarly as in FIG. 5A, it may be seen that for 0% v/v formamide, a temperature of about 77° C. corresponds to the Tm of duplexes formed by hybridization between cP7 and the P7 standard library capture primers (curve 503), while a temperature of about 91° C. corresponds to the Tm of duplexes formed by hybridization between cP7 and LNA-modified P7 capture primers (curve 504). As the concentration of formamide increases, the Tms decrease both for duplexes formed by hybridization between cP7 and the P7 standard library capture primers and for duplexes formed by hybridization between cP7 and LNA-modified P7 capture primers. For example, at a concentration of about 5% v/v formamide, the Tm of duplexes formed by hybridization between cP7 and the P7 standard library capture primers decreases to about 69° C., and the Tm of duplexes formed by hybridization between cP7 and LNA-modified P7 capture primers decreases to about 88° C. At a concentration of about 10% v/v formamide, the Tm of duplexes formed by hybridization between cP7 and the P7 standard library capture primers decreases to about 66° C., and the Tm of duplexes formed by hybridization between cP7 and LNA-modified P7 capture primers decreases to about 85° C. At a concentration of about 15% v/v formamide, the Tm of duplexes formed by hybridization between cP7 and the P7 standard library capture primers decreases to about 63° C., and the Tm of duplexes formed by hybridization between cP7 and LNA-modified P7 capture primers decreases to about 82° C. At a concentration of about 20% v/v formamide, the Tm of duplexes formed by hybridization between cP7 and the P7 standard library capture primers decreases to about 58° C., and the Tm of duplexes formed by hybridization between cP7 and LNA-modified P7 capture primers decreases to about 79° C.

Accordingly, from FIG. 5B it may be understood that at any given concentration of formamide (e.g., at a concentration of about 1% to about 20% formamide (% v/v), or about 5% to about 20% formamide (% v/v)), there is a range of temperatures at which hybridization between cP7 and the P7 standard library capture primers may be substantially completely inhibited, while hybridization between cP7 and LNA-modified P7 capture primers forms highly stable duplexes. As such, within this temperature range, template polynucleotides may be captured from solution with high efficiency and with substantially no competition from solution-based annealing processes such as described with reference to FIG. 2C. It may be expected that any other capture primer and adapter sequences will exhibit a similar dependence of duplex formation upon formamide concentration.

As another example, in the nonlimiting example shown in FIG. 5C, the Tms for duplexes formed by hybridization between cP7 and the P7 standard library capture primers (curve 505) and for duplexes formed by hybridization between cP7 and LNA-modified P7 capture primers (curve 506) are shown as a function of salt concentration (mM Na+). It may be seen that for 750 mM Na+, a temperature of about 72° C. corresponds to the Tm of duplexes formed by hybridization between cP7 and the P7 standard library capture primers (curve 505), while a temperature of about 89° C. corresponds to the Tm of duplexes formed by hybridization between cP7 and LNA-modified P7 capture primers (curve 506). As the concentration of salt decreases, the Tms decrease both for duplexes formed by hybridization between cP7 and the P7 standard library capture primers and for duplexes formed by hybridization between cP7 and LNA-modified P7 capture primers. For example, at a concentration of about 500 mM Na+, the Tm of duplexes formed by hybridization between cP7 and the P7 standard library capture primers decreases to about 70° C., and the Tm of duplexes formed by hybridization between cP7 and LNA-modified P7 capture primers decreases to about 87° C. At a concentration of about 100 mM Na+, the Tm of duplexes formed by hybridization between cP7 and the P7 standard library capture primers decreases to about 55° C., and the Tm of duplexes formed by hybridization between cP7 and LNA-modified P7 capture primers decreases to about 77° C. At a concentration of about 0 mM Na+, the Tm of duplexes formed by hybridization between cP7 and the P7 standard library capture primers decreases to about 42° C., and the Tm of duplexes formed by hybridization between cP7 and LNA-modified P7 capture primers decreases to about 58° C.

Accordingly, from FIG. 5C it may be understood that at any given concentration of salt, (e.g., at a concentration of about 100 to about 800 mM Na+, or a concentration of 200 to about 800 mM Na+), there is a range of temperatures at which hybridization between cP7 and the P7 standard library capture primers may be substantially completely inhibited, while hybridization between cP7 and LNA-modified P7 capture primers forms highly stable duplexes. As such, within this temperature range, template polynucleotides may be captured from solution with high efficiency and with substantially no competition from solution-based annealing processes such as described with reference to FIG. 2C. It may be expected that any other capture primer and adapter sequences will exhibit a similar dependence of duplex formation upon salt concentration.

Figure 6:
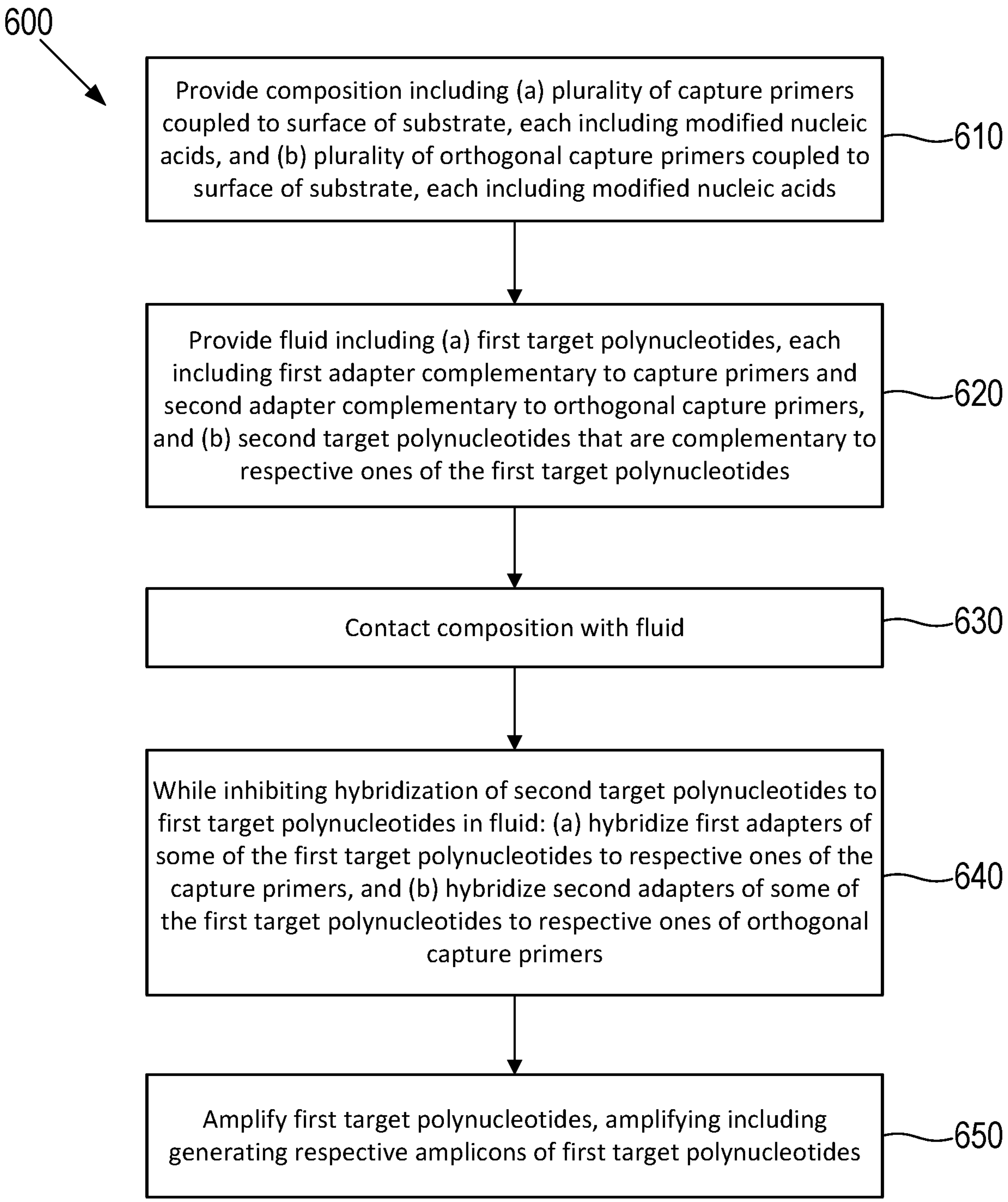
FIG. 6 illustrates an example flow of operations in a method for capturing and amplifying a polynucleotide using the present capture primers.

It will be appreciated that example compositions such as described herein may be used in any suitable method for capturing and amplifying a polynucleotide. For example, FIG. 6 illustrates an example flow of operations in a method 600 for capturing and amplifying a polynucleotide using the present modified primers. Although method 600 may be implemented using composition 3000 described with reference to FIGS. 3A-3H, method 600 may be implemented using any other suitable composition.

Referring now to FIG. 6, method 600 may include providing a composition including (a) a plurality of capture primers coupled to the surface of the substrate, each capture primer including modified nucleic acids; and (b) a plurality of orthogonal capture primers coupled to the surface of the substrate, each orthogonal capture primer including modified nucleic acids (operation 610). The composition may be similar to composition 3000 described with reference to FIG. 3A, e.g., may include capture primers 331 and orthogonal capture primers 332 coupled to substrate 300.

Method 600 illustrated in FIG. 6 further may include providing a fluid including (a) first target polynucleotides, each including a first adapter that is complementary to the capture primers and a second adapter that is complementary to the orthogonal capture primers; and (b) second target polynucleotides that are complementary to respective ones of the first target polynucleotides. The fluid may be configured similarly as described with reference to FIG. 3A, e.g., may include target polynucleotides 311, 312, 313, each of which is coupled to a first adapter 321 and a second adapter 322, and may include complementary target polynucleotides 311', 312' 313', each of which is coupled to a complementary first adapter 321' and a complementary second adapter 322'.

Method 600 illustrated in FIG. 6 further may include contacting the composition with the fluid (operation 630). For example, the composition provided in operation 610 may be contacted with the fluid provided in operation 620. Illustratively, the composition may be provided in a flowcell, and the fluid flowed into contact with the composition within the flowcell.

Method 600 illustrated FIG. 6 further may include, while inhibiting hybridization of the second target polynucleotides to the first target polynucleotides in the fluid, (a) hybridizing the first adapters of some of the first target polynucleotides to respective ones of the capture primers to form first duplexes and (b) hybridizing the second adapters of some of the first target polynucleotides to respective ones of the orthogonal capture primers to form second duplexes (operation 640). For example, in a manner such as described with reference to FIGS. 3B-3C, the hybridizations of the first adapters to capture primers and the of the second adapters to orthogonal capture primers may be performed under conditions that inhibit the first and second target polynucleotides from annealing to each other. Example conditions are provided elsewhere herein. Note that the same set of conditions may be used to cause dissociation of the first and second polynucleotides from one another and to promote hybridization of the adapters of the first polynucleotides to the present capture primers. In comparison, using previously known capture primers may involve two sets of conditions, the first condition to cause dissociation of the first and second polynucleotides from one another, followed by the second condition to promote hybridization of the adapters of the first polynucleotides to the previously known capture primers.

Method 600 illustrated in FIG. 6 further may include amplifying the first target polynucleotides, the amplifying comprising generating respective amplicons of the first target polynucleotides (operation 650). Non-limiting examples of the manner in which such amplicons may be generated are provided with reference to FIGS. 3D-3H.

Accordingly, whereas previously known capture primers may used under conditions at which non-productive rehybridization complexes may form in solution, the present modified capture primers (including orthogonal capture primers) overcome this problem by using sequences that include modified nucleic acids that impart stronger binding (and higher Tm) for surface/solution duplexes as compared to solution/solution duplexes. The difference in Tm between surface/solution and solution/solution duplexes may be achieved by using modified capture primer sequences that may, for example, include LNA, PNA, super T, or any combination of these. By incorporating base modifications to the capture primers, a temperature regime exists in which the adapters of target polynucleotides are able to hybridize to the surface but not able to hybridize to other adapters in solution.

As such, the present modified capture primers provide one or more of the following benefits:

A) Library capture is more efficient. In appropriate cases, lower input concentration of target polynucleotides may be used;

B) Surface capture post "on flowcell" denaturation may be carried out at higher temperatures, which may reduce or eliminate the need to integrate active cooling in order to reach temperatures favoring hybridization in a timely manner; and/or C) Flowcells which require a large about of library may utilize multiple fluidic pushes for seeding, which greatly increases turnaround time (TAT), e.g., time from the beginning of sample prep to obtaining sequencing data. With the higher seeding efficiency provided by the present capture primers, it is possible to use higher concentrations of target polynucleotides with fewer fluidic pushes. This may save time during seeding.

It will be appreciated that the present compositions and methods are not limited to use with the particular operations described above. For example, although FIGS. 3A-3H may be considered to described operations consistent with "bridge amplification" or "surface-bound polymerase chain reaction," it will be appreciated that the present compositions and methods readily may be adapted for use with other amplification modalities. One such amplification modality is "exclusion amplification," or ExAmp. Exclusion amplification methods may allow for the amplification of a single target polynucleotide per substrate region and the production of a substantially monoclonal population of amplicons in a substrate region. For example, the rate of amplification of the first captured target polynucleotide within a substrate region may be rapid relative to much slower rates of transport and capture of target polynucleotides at the substrate region. As such, the first target polynucleotide captured in a substrate region may be amplified rapidly and fill the entire substrate region, thus inhibiting the capture of additional target polynucleotide in the same substrate region. Alternatively, if a second target polynucleotide attaches to same substrate region after the first polynucleotide, the relatively rapid amplification of the first polynucleotide may fill enough of the substrate region to result in a signal that is sufficiently strong to perform sequencing by synthesis. The use of exclusion amplification may also result in super-Poisson distributions of monoclonal substrate regions; that is, the fraction of substrate regions in an array that are substantially monoclonal may exceed the fraction predicted by the Poisson distribution.

Increasing super-Poisson distributions of useful clusters is useful because more substantially monoclonal substrate regions may result in higher quality signal, and thus improved SBS; however, the seeding of target polynucleotides into substrate regions may follow a spatial Poisson distribution, where the trade-off for increasing the number of occupied substrate regions is increasing the number of polyclonal substrate regions. One method of obtaining higher super-Poisson distributions is to have seeding occur quickly, followed by a delay among the seeded target polynucleotide. The delay, termed "kinetic delay" because it is thought to arise through the biochemical reaction kinetics, gives one seeded target polynucleotide an earlier start over the other seeded targets. Exclusion amplification works by using recombinase to facilitate the invasion of primers (e.g., primers attached to a substrate region) into double-stranded DNA (e.g., a target polynucleotide) when the recombinase mediates a sequence match. The present compositions and methods may be adapted for use with recombinase to facilitate the invasion of the present capture primers and orthogonal capture primers into the target polynucleotides when the recombinase mediates a sequence match. Indeed, the present compositions and methods may be adapted for use with any surface-based polynucleotide amplification methods such as thermal PCR, chemically denatured PCR, and enzymatically mediated methods (which may also be referred to as recombinase polymerase amplification (RPA) or ExAmp).

Additional Comments

While various illustrative examples are described above, it will be apparent to one skilled in the art that various changes and modifications may be made therein without departing from the invention. The appended claims are intended to cover all such changes and modifications that fall within the true spirit and scope of the invention.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

What is claimed is:

1. A composition for capturing first target polynucleotides on a surface of a substrate, the composition comprising:
 - a plurality of capture primers coupled to the surface of the substrate, each of the capture primers comprising modified nucleic acids; and
 - a plurality of orthogonal capture primers coupled to the surface of the substrate, each of the orthogonal capture primers comprising modified nucleic acids,
 - first target polynucleotides, wherein each of the first target polynucleotides comprises a first adapter that is complementary to the capture primers, and a second adapter that is complementary to the orthogonal capture primers, wherein the first adapter and the second adapter are located in different locations of each of the first target polynucleotides and have different nucleotide sequences;
 - second target polynucleotides that are complementary to the first target polynucleotides,
 - wherein the first adapter of some of the first target polynucleotides is hybridized to the capture primers, thereby forming first duplexes on the surface of the substrate, and wherein the second adapter of some of the first target polynucleotides is hybridized to the orthogonal capture primers, thereby forming second duplexes on the surface of the substrate; and
 - wherein each of the first duplexes and each of the second duplexes has a melting temperature (Tm) that is greater than a Tm of third duplexes that are formed by hybridization of the second target polynucleotides to the first target polynucleotides.

2. The composition of claim 1, wherein the modified nucleic acids of the capture primers comprise locked nucleic acid (LNA), peptide nucleic acid (PNA), or 5-hydroxylbutynl-2'-deoxyuridine.

3. The composition of claim 1, wherein the capture primers further comprise deoxyribonucleic acid (DNA).

4. The composition of claim 3, wherein the modified nucleic acids and the DNA are distributed between 5' end and 3' end of each of the capture primers.

5. The composition of claim 3, wherein the modified nucleic acids are disposed at 5' end of each of the capture primers and the DNA is disposed at 3' end of each of the capture primers.

6. The composition of claim 1, wherein the modified nucleic acids of the orthogonal capture primers comprise locked nucleic acid (LNA), peptide nucleic acid (PNA), or 5-hydroxylbutynl-2'-deoxyuridine.

7. The composition of claim 6, wherein the orthogonal capture primers further comprise deoxyribonucleic acid (DNA).

8. The composition of claim 7, wherein the modified nucleic acids and the DNA are distributed between 5' end and 3' end of each of the orthogonal capture primers.

9. The composition of claim 7, wherein the modified nucleic acids are disposed at 5' end of each of the orthogonal capture primers and the DNA is disposed at 3' end of each of the orthogonal capture primers.

10. The composition of claim 1, wherein each of the first duplexes has a melting temperature (Tm) between about 80° C. and about 110° C., and each of the second duplexes has a melting temperature (Tm) between about 80° C. and about 110° C.

11. The composition of claim 1, wherein each of the first duplexes has a melting temperature (Tm) is between about 85° C. and about 105° C., and each of the second duplexes has a melting temperature (Tm) between about 85° C. and about 105° C.

12. The composition of claim 1, wherein each of the first duplexes has a melting temperature (Tm) between about 90°

C. and about 100° C., and each of the second duplexes has a melting temperature (Tm) between about 90° C. and about 100° C.

13. The composition of claim 1, wherein the hybridization of the first adapters of some of the first target polynucleotides to the capture primers, and the hybridization of the second adapters of some of the first target polynucleotides to the orthogonal capture primers occur under a condition that inhibits hybridization of the second target polynucleotides to the first target polynucleotides.

14. The composition of claim 1, further comprising about 1% to about 100% formamide (% v/v).

15. The composition of claim 1, further comprising about 5% to about 80% formamide (% v/v).

16. The composition of claim 1, further comprising about 100 to about 800 mM Na+.

17. The composition of claim 1, further comprising about 200 to about 800 mM Na+.

18. The composition of claim 1, wherein the capture primers are modified P5 capture primers, and wherein the orthogonal capture primers are modified P7 capture primers.

19. The composition of claim 1, wherein each of the capture primers includes about five to about twenty of the modified nucleic acids, and wherein each of the orthogonal capture primers includes about five to about twenty of the modified nucleic acids.

20. The composition of claim 1, wherein each of the capture primers includes at least about nine of the modified nucleic acids, and wherein each of the orthogonal capture primers includes at least about nine of the modified nucleic acids.

21. The composition of claim 1, wherein each of the capture primers includes at least about twelve of the modified nucleic acids, and wherein each of the orthogonal capture primers includes at least about twelve of the modified nucleic acids.

22. The composition of claim 1, wherein each of the capture primers includes at least about fifteen of the modified nucleic acids, and wherein each of the orthogonal capture primers includes at least about fifteen of the modified nucleic acids.

23. A method for capturing and amplifying first target polynucleotides on a surface of a substrate, the method comprising:

providing a composition comprises:

a plurality of capture primers coupled to the surface of the substrate, each of the capture primers comprising modified nucleic acids; and a plurality of orthogonal capture primers coupled to the surface of the substrate, each of the orthogonal capture primers comprising modified nucleic acids;

providing a fluid comprises:

first target polynucleotides, wherein each of the first target polynucleotides comprises a first adapter that is complementary to the capture primers and a second adapter that is complementary to the orthogonal capture primers; and second target polynucleotides that are complementary to the first target polynucleotides;

contacting the composition with the fluid under a condition that inhibits hybridization of the second target polynucleotides to the first target polynucleotides forming first duplexes on the surface of the substrate by hybridizing the first adapter of some of the first target polynucleotides to the capture primers;

forming second duplexes on the surface of the substrate by hybridizing the second adapter of some of the first target polynucleotides to the orthogonal capture primers; and then generating amplicons of the first target polynucleotides by amplifying the first target polynucleotides of the first duplexes and/or the second duplexes, wherein each of the first duplexes and each of the second duplexes has a melting temperature (Tm) that is greater than a Tm of third duplexes that are formed by hybridization of the second target polynucleotides to the first target polynucleotides.

* * * * *

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: P5 capture primer

<400> SEQUENCE: 1

aatgatacgg cgaccaccga                                                20


<210> SEQ ID NO 2
<211> LENGTH: 21
<212> TYPE: DNA
<213> ORGANISM: Artificial Sequence
<220> FEATURE:
<223> OTHER INFORMATION: P7 capture primer

<400> SEQUENCE: 2

caagcagaag acggcatacg a                                              21


<210> SEQ ID NO 3
<211> LENGTH: 20
```

-continued

<212> TYPE: DNA
<213> ORGANISM: Artificial Sequence
<220> FEATURE:
<223> OTHER INFORMATION: Complementary P5 adapter

<400> SEQUENCE: 3
tcggtggtcg ccgtatcatt 20

<210> SEQ ID NO 4
<211> LENGTH: 21
<212> TYPE: DNA
<213> ORGANISM: Artificial Sequence
<220> FEATURE:
<223> OTHER INFORMATION: Complementary P7 adapter

<400> SEQUENCE: 4
tcgtatgccg tcttctgctt g 21

<210> SEQ ID NO 5
<211> LENGTH: 35
<212> TYPE: DNA
<213> ORGANISM: Artificial Sequence
<220> FEATURE:
<223> OTHER INFORMATION: High Tm DNA/LNA chimeric P5/P7-Standard P5
<220> FEATURE:
<221> NAME/KEY: misc_feature
<222> LOCATION: (29)..(29)
<223> OTHER INFORMATION: n = u

<400> SEQUENCE: 5
ttttttaatg atacggcgac caccgaganc tacac 35

<210> SEQ ID NO 6
<211> LENGTH: 35
<212> TYPE: DNA
<213> ORGANISM: Artificial Sequence
<220> FEATURE:
<223> OTHER INFORMATION: High Tm DNA/LNA chimeric P5/P7-LNA-mod. P5
<220> FEATURE:
<221> NAME/KEY: misc_feature
<222> LOCATION: (7)..(21)
<223> OTHER INFORMATION: Locked Nucleic Acid (LNA)
<220> FEATURE:
<221> NAME/KEY: misc_feature
<222> LOCATION: (29)..(29)
<223> OTHER INFORMATION: n = u

<400> SEQUENCE: 6
ttttttaatg atacggcgac caccgaganc tacac 35

<210> SEQ ID NO 7
<211> LENGTH: 35
<212> TYPE: DNA
<213> ORGANISM: Artificial Sequence
<220> FEATURE:
<223> OTHER INFORMATION: High Tm DNA/LNA chimeric P5/P7-LNA-mod. P5
<220> FEATURE:
<221> NAME/KEY: misc_feature
<222> LOCATION: (7)..(18)
<223> OTHER INFORMATION: Locked Nucleic Acid (LNA)
<220> FEATURE:
<221> NAME/KEY: misc_feature
<222> LOCATION: (29)..(29)
<223> OTHER INFORMATION: n = u

<400> SEQUENCE: 7
ttttttaatg atacggcgac caccgaganc tacac 35

<210> SEQ ID NO 8

-continued

<211> LENGTH: 35
<212> TYPE: DNA
<213> ORGANISM: Artificial Sequence
<220> FEATURE:
<223> OTHER INFORMATION: High Tm DNA/LNA chimeric P5/P7-LNA-mod. P5
<220> FEATURE:
<221> NAME/KEY: misc_feature
<222> LOCATION: (7)..(15)
<223> OTHER INFORMATION: Locked Nucleic Acid (LNA)
<220> FEATURE:
<221> NAME/KEY: misc_feature
<222> LOCATION: (29)..(29)
<223> OTHER INFORMATION: n = u

<400> SEQUENCE: 8 tttttaatg atacggcgac caccgaganc tacac 35

<210> SEQ ID NO 9
<211> LENGTH: 30
<212> TYPE: DNA
<213> ORGANISM: Artificial Sequence
<220> FEATURE:
<223> OTHER INFORMATION: High Tm DNA/LNA chimeric P5/P7-Standard P7
<220> FEATURE:
<221> NAME/KEY: misc_feature
<222> LOCATION: (26)..(26)
<223> OTHER INFORMATION: n = 8-oxoG

<400> SEQUENCE: 9
ttttttcaag cagaagacgg catacnagat 30

<210> SEQ ID NO 10
<211> LENGTH: 30
<212> TYPE: DNA
<213> ORGANISM: Artificial Sequence
<220> FEATURE:
<223> OTHER INFORMATION: High Tm DNA/LNA chimeric P5/P7-LNA-mod. P7
<220> FEATURE:
<221> NAME/KEY: misc_feature
<222> LOCATION: (7)..(21)
<223> OTHER INFORMATION: Locked Nucleic Acid (LNA)
<220> FEATURE:
<221> NAME/KEY: misc_feature
<222> LOCATION: (26)..(26)
<223> OTHER INFORMATION: n = 8-oxoG

<400> SEQUENCE: 10
ttttttcaag cagaagacgg catacnagat 30

<210> SEQ ID NO 11
<211> LENGTH: 30
<212> TYPE: DNA
<213> ORGANISM: Artificial Sequence
<220> FEATURE:
<223> OTHER INFORMATION: High Tm DNA/LNA chimeric P5/P7-LNA-mod. P7
<220> FEATURE:
<221> NAME/KEY: misc_feature
<222> LOCATION: (7)..(18)
<223> OTHER INFORMATION: Locked Nucleic Acid (LNA)
<220> FEATURE:
<221> NAME/KEY: misc_feature
<222> LOCATION: (26)..(26)
<223> OTHER INFORMATION: n = 8-oxoG

<400> SEQUENCE: 11
ttttttcaag cagaagacgg catacnagat 30

<210> SEQ ID NO 12
<211> LENGTH: 30
<212> TYPE: DNA
<213> ORGANISM: Artificial Sequence -continued

```
<220> FEATURE:
<223> OTHER INFORMATION: High Tm DNA/LNA chimeric P5/P7-LNA-mod. P7
<220> FEATURE:
<221> NAME/KEY: misc_feature
<222> LOCATION: (7)..(15)
<223> OTHER INFORMATION: Locked Nucleic Acid (LNA)
<220> FEATURE:
<221> NAME/KEY: misc_feature
<222> LOCATION: (26)..(26)
<223> OTHER INFORMATION: n = 8-oxoG

<400> SEQUENCE: 12

tttttcaag cagaagacgg catacnagat                                30


<210> SEQ ID NO 13
<211> LENGTH: 24
<212> TYPE: DNA
<213> ORGANISM: Artificial Sequence
<220> FEATURE:
<223> OTHER INFORMATION: LNA-modified P7 capture primer
<220> FEATURE:
<221> NAME/KEY: misc_feature
<222> LOCATION: (1)..(15)
<223> OTHER INFORMATION: Locked Nucleic Acid (LNA)
<220> FEATURE:
<221> NAME/KEY: misc_feature
<222> LOCATION: (20)..(20)
<223> OTHER INFORMATION: n = 8-oxoG

<400> SEQUENCE: 13

caagcagaag acggcatacn agat                                     24
```